United States Patent [19]
Berkowitz et al.

[11] Patent Number: 5,459,237
[45] Date of Patent: Oct. 17, 1995

[54] PEPTIDE COMPOSITIONS AND USES THEREFOR

[75] Inventors: Barry Berkowitz, Ft. Washington; W. Lee Maloy; U. Prasad Kari, both of Lansdale, all of Pa.

[73] Assignee: Magainin Pharmaceuticals Inc., Plymouth Meeting, Pa.

[21] Appl. No.: 908,455

[22] Filed: Jul. 2, 1992

Related U.S. Application Data

[63] Continuation-in-part of Ser. No. 686,115, Apr. 15, 1991, abandoned, which is a continuation-in-part of Ser. No. 476,629, Feb. 8, 1990, abandoned.

[51] Int. Cl.⁶ .......................... C07K 14/00; A61K 38/16
[52] U.S. Cl. .................. 530/326; 530/324; 530/325; 530/327
[58] Field of Search ................... 530/324–327; 514/12–14

[56] References Cited

U.S. PATENT DOCUMENTS

| | | | |
|---|---|---|---|
| 4,107,298 | 8/1978 | Lunig | 530/326 |
| 4,617,149 | 10/1986 | DiMarchi et al. | 530/324 |
| 4,636,489 | 1/1987 | Seemuller et al. | 530/324 |
| 4,659,692 | 4/1987 | Lehrer et al. | 530/324 |
| 4,668,662 | 5/1987 | Tripier | 530/324 |
| 4,791,100 | 12/1988 | Kramer et al. | 530/324 |
| 4,962,277 | 10/1990 | Cuervo et al. | 514/14 |

FOREIGN PATENT DOCUMENTS 04371  5/1989  WIPO.

OTHER PUBLICATIONS

Mihara, et al., Peptide Chemistry (1985), pp. 223–228.
Lee, et al., Peptide Chemistry (1985), pp. 317–320.

*Primary Examiner*—Jill Warden
*Assistant Examiner*—Carol A. Salata
*Attorney, Agent, or Firm*—Finnegan, Henderson, Farabow, Garrett & Dunner

[57] ABSTRACT

A biologically active amphiphilic peptide which in accordance with an aspect of the present invention, includes one of the following basic structures $X_1$ through $X_7$, wherein:

$X_1$ is $-[R_1-R_2-R_2-R_3-R_1-R_2-R_2]-_n$
$X_2$ is $-[R_2-R_2-R_3-R_1-R_2-R_2-R_1]-_n$;
$X_3$ is $-[R_2-R_3-R_1-R_2-R_2-R_1-R_2]-_n$;
$X_4$ is $-[R_3-R_1-R_2-R_2-R_1-R_2-R_2]-_n$;
$X_5$ is $-[R_1-R_2-R_2-R_1-R_2-R_2-R_3]-_n$;
$X_6$ is $-[R_2-R_2-R_1-R_2-R_2-R_3-R_1]-_n$; and
$X_7$ is $-[R_2-R_1-R_2-R_2-R_3-R_1-R_2]-_n$;

wherein $R_1$ is a basic hydrophilic amino acid, $R_2$ is a hydrophobic amino acid, $R_3$ is a neutral hydrophilic, basic hydrophilic or hydrophobic amino acid and n is from 2 to 5.

8 Claims, No Drawings

SEQUENCE LISTING ( 1 ) GENERAL INFORMATION:

( i i i ) NUMBER OF SEQUENCES: 89

( 2 ) INFORMATION FOR SEQ ID NO:1:

( i ) SEQUENCE CHARACTERISTICS:

(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide- terminated (xi) SEQUENCE DESCRIPTION: SEQ ID NO:1:

Lys Ile Ala Gly Lys Ile Ala Lys Ile Ala
 5                   10
Gly Lys Ile Ala Lys Ile Ala Gly Lys Ile
15                   20
Ala (2) INFORMATION FOR SEQ ID NO:2:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide- terminated (xi) SEQUENCE DESCRIPTION: SEQ ID NO:2:

Lys Ile Ala Lys Ile Ala Gly Lys Ile Ala
 5                   10
Lys Ile Ala Gly Lys Ile Ala Lys Ile Ala
15                   20
Gly (2) INFORMATION FOR SEQ ID NO:3:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide- terminated (xi) SEQUENCE DESCRIPTION: SEQ ID NO:3:

Lys Ile Ala Gly Lys Ile Gly Lys Ile Ala
 5                   10
Gly Lys Ile Gly Lys Ile Ala Gly Lys Ile
15                   20
Gly (2) INFORMATION FOR SEQ ID NO:4:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide- terminated (xi) SEQUENCE DESCRIPTION: SEQ ID NO:4:

Lys Leu Ala Gly Lys Leu Ala Lys Leu Ala
 5                   10
Gly Lys Leu Ala Lys Leu Ala Gly Lys Leu
15                   20
Ala (2) INFORMATION FOR SEQ ID NO:5:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:5:

```
Lys Phe Ala Gly Lys Phe Ala Lys Phe Ala
 5                   10
Gly Lys Phe Ala Lys Phe Ala Gly Lys Phe
15                   20
Ala
```

( 2 ) INFORMATION FOR SEQ ID NO:6:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:6:

```
Lys Ala Leu Ser Lys Ala Leu Lys Ala Leu
 5                   10
Ser Lys Ala Leu Lys Ala Leu Ser Lys Ala
15                   20
Leu
```

( 2 ) INFORMATION FOR SEQ ID NO:7:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:7:

```
Lys Leu Leu Lys Ala Leu Gly Lys Leu Leu
 5                   10
Lys Ala Leu Gly Lys Leu Leu Lys Ala Leu
15                   20
Gly
```

( 2 ) INFORMATION FOR SEQ ID NO:8:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:8:

```
Lys Ala Ile Gly Lys Ala Ile Lys Ala Ile
 5                   10
Gly Lys Ala Ile Lys Ala Ile Gly Lys Ala
15                   20
Ile
```

( 2 ) INFORMATION FOR SEQ ID NO:9:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:9:

```
Gly Ile Ala Lys Ile Ala Lys Gly Ile Ala
 5                        10
Lys Ile Ala Lys Gly Ile Ala Lys Ile Ala
15                        20
Lys
```

( 2 ) INFORMATION FOR SEQ ID NO:10:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:10:

```
Lys Ile Ala Lys Ile Phe Gly Lys Ile Ala
 5                        10
Lys Ile Phe Gly Lys Ile Ala Lys Ile Phe
15                        20
Gly
```

( 2 ) INFORMATION FOR SEQ ID NO:11:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:11:

```
Gly Ile Ala Arg Ile Ala Lys Gly Ile Ala
 5                        10
Arg Ile Ala Lys Gly Ile Ala Arg Ile Ala
15                        20
Lys
```

( 2 ) INFORMATION FOR SEQ ID NO:12:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:12:

```
Lys Phe Ala Arg Ile Ala Gly Lys Phe Ala
 5                        10
Arg Ile Ala Gly Lys Phe Ala Arg Ile Ala
15                        20
Gly
```

( 2 ) INFORMATION FOR SEQ ID NO:13:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:13:

```
Gly  Phe  Ala  Lys  Ile  Ala  Lys  Gly  Phe  Ala
 5                              10
Lys  Ile  Ala  Lys  Gly  Phe  Ala  Lys  Ile  Ala
15                              20
Lys
```

( 2 ) INFORMATION FOR SEQ ID NO:14:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated, Xaa is ornithine ( x i ) SEQUENCE DESCRIPTION: SEQ ID NO:14:

```
Lys  Ile  Ala  Gly  Xaa  Ile  Ala  Lys  Ile  Ala
 5                              10
Gly  Xaa  Ile  Ala  Lys  Ile  Ala  Gly  Xaa  Ile
15                              20
Ala
```

( 2 ) INFORMATION FOR SEQ ID NO:15:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:15:

```
Lys  Ile  Ala  Arg  Ile  Ala  Gly  Lys  Ile  Ala
 5                              10
Arg  Ile  Ala  Gly  Lys  Ile  Ala  Arg  Ile  Ala
 5                              20
Gly
```

( 2 ) INFORMATION FOR SEQ ID NO:16:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated, Xaa is ornithine ( x i ) SEQUENCE DESCRIPTION: SEQ ID NO:16:

```
Xaa  Ile  Ala  Gly  Lys  Ile  Ala  Xaa  Ile  Ala
 5                              10
Gly  Lys  Ile  Ala  Xaa  Ile  Ala  Gly  Lys  Ile
```

```
                      1 5                    2 0
                      Ala
```

( 2 ) INFORMATION FOR SEQ ID NO:17:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:17:

```
                      Gly  Ile  Ala  Arg  Ile  Phe  Lys  Gly  Ile  Ala
                      5                         1 0
                      Arg  Ile  Phe  Lys  Gly  Ile  Ala  Arg  Ile  Phe
                      1 5                       2 0
                      Lys
```

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated, Xaa is
            norleucine ( x i ) SEQUENCE DESCRIPTION: SEQ ID NO:18:

```
                      Lys  Xaa  Ala  Gly  Lys  Xaa  Ala  Lys  Xaa  Ala
                      5                         1 0
                      Gly  Lys  Xaa  Ala  Lys  Xaa  Ala  Gly  Lys  Xaa
                      1 5                       2 0
                      Ala
```

( 2 ) INFORMATION FOR SEQ ID NO:19:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated, Xaa is
            norleucine ( x i ) SEQUENCE DESCRIPTION: SEQ ID NO:19:

```
                      Lys  Xaa  Ala  Gly  Lys  Ile  Ala  Lys  Xaa  Ala
                      5                         1 0
                      Gly  Lys  Ile  Ala  Lys  Xaa  Ala  Gly  Lys  Ile
                      1 5                       2 0
                      Ala
```

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated, Xaa is
            norleucine (xi) SEQUENCE DESCRIPTION: SEQ ID NO:20:

```
Lys  Ile  Ala  Gly  Lys  Xaa  Ala  Lys  Ile  Ala
 5                              10
Gly  Lys  Xaa  Ala  Lys  Ile  Ala  Gly  Lys  Xaa
15                              20
Ala
```

(2) INFORMATION FOR SEQ ID NO:21:

- (i) SEQUENCE CHARACTERISTICS:
    - (A) LENGTH: 21 amino acids
    - (B) TYPE: amino acid
    - (C) STRANDEDNESS:
    - (D) TOPOLOGY: linear

- (ii) MOLECULE TYPE: peptide

- (ix) FEATURE:
    - (D) OTHER INFORMATION: amide- terminated, Xaa is norvaline (xi) SEQUENCE DESCRIPTION: SEQ ID NO:21:

```
Lys  Xaa  Ala  Gly  Lys  Xaa  Ala  Lys  Xaa  Ala
 5                              10
Gly  Lys  Xaa  Ala  Lys  Xaa  Ala  Gly  Lys  Xaa
15                              20
Ala
```

(2) INFORMATION FOR SEQ ID NO:22:

- (i) SEQUENCE CHARACTERISTICS:
    - (A) LENGTH: 21 amino acids
    - (B) TYPE: amino acid
    - (C) STRANDEDNESS:
    - (D) TOPOLOGY: linear

- (ii) MOLECULE TYPE: peptide

- (ix) FEATURE:
    - (D) OTHER INFORMATION: amide- terminated, Xaa is norvaline (xi) SEQUENCE DESCRIPTION: SEQ ID NO:22:

```
Lys  Xaa  Ala  Gly  Lys  Ile  Ala  Lys  Xaa  Ala
 5                              10
Gly  Lys  Ile  Ala  Lys  Xaa  Ala  Gly  Lys  Xaa
15                              20
Ala
```

(2) INFORMATION FOR SEQ ID NO:23:

- (i) SEQUENCE CHARACTERISTICS:
    - (A) LENGTH: 21 amino acids
    - (B) TYPE: amino acid
    - (C) STRANDEDNESS:
    - (D) TOPOLOGY: linear

- (ii) MOLECULE TYPE: peptide

- (ix) FEATURE:
    - (D) OTHER INFORMATION: amide- terminated (xi) SEQUENCE DESCRIPTION: SEQ ID NO:23:

```
Lys  Leu  Leu  Ser  Lys  Leu  Gly  Lys  Leu  Leu
 5                              10
Ser  Lys  Leu  Gly  Lys  Leu  Leu  Ser  Lys  Leu
15                              20
Gly
```

(2) INFORMATION FOR SEQ ID NO:24:

- (i) SEQUENCE CHARACTERISTICS:
    - (A) LENGTH: 21 amino acids
    - (B) TYPE: amino acid
    - (C) STRANDEDNESS:
    - (D) TOPOLOGY: linear

- (ii) MOLECULE TYPE: peptide (ix) FEATURE:
  (D) OTHER INFORMATION: amide- terminated (xi) SEQUENCE DESCRIPTION: SEQ ID NO:24:

```
Lys Leu Leu Ser Lys Phe Gly Lys Leu Leu
 5                    10
Ser Lys Phe Gly Lys Leu Leu Ser Lys Phe
15                    20
Gly
```

(2) INFORMATION FOR SEQ ID NO:25:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated, Xaa is norvaline (xi) SEQUENCE DESCRIPTION: SEQ ID NO:25:

```
Lys Ile Ala Gly Lys Xaa Ala Lys Ile Ala
 5                    10
Gly Lys Xaa Ala Lys Ile Ala Gly Lys Xaa
15                    20
Ala
```

(2) INFORMATION FOR SEQ ID NO:26:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated (xi) SEQUENCE DESCRIPTION: SEQ ID NO:26:

```
His Ile Ala Gly His Ile Ala His Ile Ala
 5                    10
Gly His Ile Ala His Ile Ala Gly His Ile
15                    20
Ala
```

(2) INFORMATION FOR SEQ ID NO:27:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated (xi) SEQUENCE DESCRIPTION: SEQ ID NO:27:

```
Ala Gly Lys Ile Ala Lys Ile Ala Gly Lys
 5                    10
Ile Ala Lys Ile Ala Gly Lys Ile Ala Lys
15                    20
Ile
```

(2) INFORMATION FOR SEQ ID NO:28:

(i) SEQUENCE CHARACTERISTICS:
    (A) LENGTH: 21 amino acids
    (B) TYPE: amino acid
    (C) STRANDEDNESS:
    (D) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:28:

```
Ile Ala Lys Ile Ala Gly Lys Ile Ala Lys
 5                      10
Ile Ala Gly Lys Ile Ala Lys Ile Ala Gly
15                      20
Lys
```

( 2 ) INFORMATION FOR SEQ ID NO:29:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:29:

```
Lys Ile Ala Gly Arg Ile Ala Lys Ile Ala
 5                      10
Gly Arg Ile Ala Lys Ile Ala Gly Arg Ile
15                      20
Ala
```

( 2 ) INFORMATION FOR SEQ ID NO:30:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:30:

```
Arg Ile Ala Gly Arg Ile Ala Arg Ile Ala
 5                      10
Gly Arg Ile Ala Arg Ile Ala Gly Arg Ile
15                      20
Ala
```

( 2 ) INFORMATION FOR SEQ ID NO:31:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:31:

```
Lys Val Ala Gly Lys Ile Ala Lys Val Ala
 5                      10
Gly Lys Ile Ala Lys Val Ala Gly Lys Ile
15                      20
Ala
```

( 2 ) INFORMATION FOR SEQ ID NO:32:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:32:
Lys Ile Ala Gly Lys Val Ala Lys Ile Ala
 5                          10
Gly Lys Val Ala Lys Ile Ala Gly Lys Val
15                          20
Ala ( 2 ) INFORMATION FOR SEQ ID NO:33:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:33:
Ala Lys Ile Ala Gly Lys Ile Ala Lys Ile
 5                          10
Ala Gly Lys Ile Ala Lys Ile Ala Gly Lys
15                          20
Ile ( 2 ) INFORMATION FOR SEQ ID NO:34:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated, Xaa is
        ornithine ( x i ) SEQUENCE DESCRIPTION: SEQ ID NO:34:
Xaa Ile Ala Gly Xaa Ile Ala Xaa Ile Ala
 5                          10
Gly Xaa Ile Ala Xaa Ile Ala Gly Xaa Ile
15                          20
Ala ( 2 ) INFORMATION FOR SEQ ID NO:35:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:35:
Lys Phe Ala Gly Lys Ile Ala Lys Phe Ala
 5                          10
Gly Lys Ile Ala Lys Phe Ala Gly Lys Ile
15                          20
Ala ( 2 ) INFORMATION FOR SEQ ID NO:36:

( i ) SEQUENCE CHARACTERISTICS:
    ( A ) LENGTH: 21 amino acids
    ( C ) STRANDEDNESS:

(B) TYPE: amino acid
(D) TOPOLOGY: linear (ii) MOLECULE TYPE: peptide (ix) FEATURE:
(D) OTHER INFORMATION: amide-terminated (xi) SEQUENCE DESCRIPTION: SEQ ID NO:36:

```
Lys Ile Ala Gly Lys Phe Ala Lys Ile Ala
 5                           10
Gly Lys Phe Ala Lys Ile Ala Gly Lys Phe
15                           20
Ala
```

(2) INFORMATION FOR SEQ ID NO:37:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide-terminated, Xaa is cyclohexylalanine (xi) SEQUENCE DESCRIPTION: SEQ ID NO:37:

```
Lys Xaa Ala Gly Lys Ile Ala Lys Xaa Ala
 5                           10
Gly Lys Ile Ala Lys Xaa Ala Gly Lys Ile
15                           20
Ala
```

(2) INFORMATION FOR SEQ ID NO:38:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide-terminated, Xaa is norleucine (xi) SEQUENCE DESCRIPTION: SEQ ID NO:38:

```
Lys Xaa Ala Lys Ile Ala Gly Lys Xaa Ala
 5                           10
Lys Ile Ala Gly Lys Xaa Ala Lys Ile Ala
15                           20
Gly
```

(2) INFORMATION FOR SEQ ID NO:39:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: amide-terminated (xi) SEQUENCE DESCRIPTION: SEQ ID NO:39:

```
Arg Ile Ala Gly Lys Ile Ala Arg Ile Ala
 5                           10
Gly Lys Ile Ala Arg Ile Ala Gly Lys Ile
15                           20
Ala
```

(2) INFORMATION FOR SEQ ID NO:40:

( i ) SEQUENCE CHARACTERISTICS:
  ( A ) LENGTH: 21 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( D ) OTHER INFORMATION: amide- terminated, Xaa is homoarginine ( x i ) SEQUENCE DESCRIPTION: SEQ ID NO:40:

```
Xaa  Ile  Ala  Gly  Xaa  Ile  Ala  Xaa  Ile  Ala
 5                       10
Gly  Xaa  Ile  Ala  Xaa  Ile  Ala  Gly  Xaa  Ile
15                       20
Ala
```

( 2 ) INFORMATION FOR SEQ ID NO:41:

( i ) SEQUENCE CHARACTERISTICS:
  ( A ) LENGTH: 21 amino acids
  ( B ) TYPE: amino acid
  ( C ) STRANDEDNESS:
  ( D ) TOPOLOGY: linear ( i i ) MOLECULE TYPE: peptide ( i x ) FEATURE: amide-terminated, Xaa is p-aminophenylalanine ( x i ) SEQUENCE DESCRIPTION: SEQ ID NO:41:

```
Xaa  Ile  Ala  Gly  Lys  Ile  Ala  Xaa  Ile  Ala
 5                       10
Gly  Lys  Ile  Ala  Xaa  Ile  Ala  Gly  Lys  Ile
15                       20
Ala
```

( 2 ) INFORMATION FOR SEQ ID NO:42:

( i ) SEQUENCE CHARACTERISTICS:
  ( A ) LENGTH: 21 amino acids
  ( B ) TYPE: amino acid
  ( C ) STRANDEDNESS:
  ( D ) TOPOLOGY: linear ( i i ) MOLECULE TYPE: peptide ( i x ) FEATURE: amide-terminated, Xaa is p-aminophenylalanine ( x i ) SEQUENCE DESCRIPTION: SEQ ID NO:42:

```
Lys  Ile  Ala  Gly  Xaa  Ile  Ala  Lys  Ile  Ala
 5                       10
Gly  Xaa  Ile  Ala  Lys  Ile  Ala  Gly  Xaa  Ile
15                       20
Ala
```

( 2 ) INFORMATION FOR SEQ ID NO:43:

( i ) SEQUENCE CHARACTERISTICS:
  ( A ) LENGTH: 24 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( D ) OTHER INFORMATION: amide- terminated ( x i ) SEQUENCE DESCRIPTION: SEQ ID NO:43:

```
Lys  Ile  Ala  Lys  Ile  Ala  Gly  Lys  Ile  Ala
 5                       10
Lys  Ile  Ala  Gly  Lys  Ile  Ala  Lys  Ile  Ala
15                       20
Gly  Lys  Ile  Ala
```

( 2 ) INFORMATION FOR SEQ ID NO:44:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:44:

```
Lys  Leu  Ala  Ser  Lys  Ala  Gly  Lys  Ile  Ala  Gly
 5                        10
Lys  Ile  Ala  Lys  Val  Ala  Leu  Lys  Ala  Leu
15                        20
```

( 2 ) INFORMATION FOR SEQ ID NO:45:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated, Xaa is ornithine ( x i ) SEQUENCE DESCRIPTION: SEQ ID NO:45:

```
Lys  Ile  Ala  Gly  Lys  Ile  Ala  Lys  Ile  Ala  Gly
 5                        10
Xaa  Ile  Ala  Lys  Ile  Ala  Gly  Lys  Ile  Ala
15                        20
```

( 2 ) INFORMATION FOR SEQ ID NO:46:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:46:

```
Lys  Ile  Ala  Gly  Lys  Ile  Ala  Lys  Ile  Ala
 5                        10
Gly  Arg  Ile  Ala  Lys  Ile  Ala  Gly  Lys  Ile
15                        20
Ala
```

( 2 ) INFORMATION FOR SEQ ID NO:47:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: amide- terminated, Xaa is norleucine.

( x i ) SEQUENCE DESCRIPTION: SEQ ID NO:47:

```
Lys  Ile  Ala  Gly  Lys  Ile  Ala  Lys  Ile  Ala
 5                        10
Gly  Xaa  Ile  Ala  Lys  Ile  Ala  Gly  Lys  Ile
15                        20
Ala
```

( 2 ) INFORMATION FOR SEQ ID NO:48:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated, Xaa is norvaline.

(xi) SEQUENCE DESCRIPTION: SEQ ID NO:48:

```
Lys Ile Ala Gly Lys Ile Ala Lys Ile Ala
 5                          10
Gly Xaa Ile Ala Lys Ile Ala Gly Lys Ile
15                          20
Ala
```

(2) INFORMATION FOR SEQ ID NO:49:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated, Xaa is ornithine.

(xi) SEQUENCE DESCRIPTION: SEQ ID NO:49:

```
Lys Phe Ala Gly Lys Phe Ala Lys Phe Ala Gly
 5                          10
Xaa Phe Ala Lys Phe Ala Gly Lys Phe Ala
15                          20
```

(2) INFORMATION FOR SEQ ID NO:50:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated, Xaa is ornithine.

(xi) SEQUENCE DESCRIPTION: SEQ ID NO:50:

```
Lys Ile Ala Gly Lys Phe Ala Lys Ile Ala
 5                          10
Gly Xaa Phe Ala Lys Ile Ala Gly Lys Phe
15                          20
Ala
```

(2) INFORMATION FOR SEQ ID NO:51:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: amide- terminated, Xaa at residues 6, 13 and 20 is norleucine; Xaa at residue 12 is ornithine (xi) SEQUENCE DESCRIPTION: SEQ ID NO:51:

```
Lys Ile Ala Gly Lys Xaa Ala Lys Ile Ala
 5                          10
```

```
           Gly  Xaa  Xaa  Ala  Lys  Ile  Ala  Gly  Lys  Xaa
            15                      20
           Ala
```

(2) INFORMATION FOR SEQ ID NO:52:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amide-termianted (xi) SEQUENCE DESCRIPTION: SEQ ID NO:52:

```
           Lys  Met  Ala  Ser  Lys  Ala  Gly  Lys  Ile  Ala
            5                        10
           Gly  Lys  Ile  Ala  Lys  Val  Ala  Leu  Lys  Ala
            15                       20
           Leu
```

(2) INFORMATION FOR SEQ ID NO:53:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amide-terminated (xi) SEQUENCE DESCRIPTION: SEQ ID NO:53:

```
           Lys  Ile  Ala  Ser  Lys  Ala  Gly  Lys  Ile  Ala
            5                        10
           Gly  Lys  Ile  Ala  Lys  Val  Ala  Leu  Lys  Ala  Leu
            15                       20
```

(2) INFORMATION FOR SEQ ID NO:54:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amide-terminated, Xaa is
            norleucine (xi) SEQUENCE DESCRIPTION: SEQ ID NO:54:

```
           Lys  Ile  Ala  Ser  Lys  Ala  Gly  Lys  Xaa  Ala
            5                        10
           Gly  Lys  Ile  Ala  Lys  Val  Ala  Leu  Lys  Ala
            15                       20
           Leu
```

(2) INFORMATION FOR SEQ ID NO:55:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: amide-terminated, Xaa is
            norleucine.

(xi) SEQUENCE DESCRIPTION: SEQ ID NO:55:

```
            Lys  Leu  Ala  Ser  Lys  Ala  Gly  Lys  Xaa  Ala
             5                         10
            Gly  Lys  Ile  Ala  Lys  Val  Ala  Leu  Lys  Ala
            15                         20
            Leu
```

( 2 ) INFORMATION FOR SEQ ID NO:56:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated, Xaa is
            norleucine.

( x i ) SEQUENCE DESCRIPTION: SEQ ID NO:56:

```
            Lys  Xaa  Ala  Ser  Lys  Ala  Gly  Lys  Xaa  Ala
             5                         10
            Gly  Lys  Ile  Ala  Lys  Val  Ala  Leu  Lys  Ala  Leu
            15                         20
```

( 2 ) INFORMATION FOR SEQ ID NO:57:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated, Xaa is
            p- aminophenylalanine.

( x i ) SEQUENCE DESCRIPTION: SEQ ID NO:57:

```
            Lys  Ile  Ala  Gly  Lys  Ile  Ala  Lys  Ile  Ala
             5                         10
            Gly  Xaa  Ile  Ala  Lys  Ile  Ala  Gly  Lys  Ile
            15
            Ala
```

( 2 ) INFORMATION FOR SEQ ID NO:58:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:58:

```
            Lys  Ile  Ala  Gly  Ala  Ile  Ala  Lys  Ile  Ala
             5                         10
            Gly  Lys  Ile  Ala  Lys  Ile  Ala  Gly  Lys  Ile
            15                         20
            Ala
```

( 2 ) INFORMATION FOR SEQ ID NO:59:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:59:

```
Lys Ile Ala Gly Lys Ile Ala Lys Ile Ala
5                             10
Gly Ala Ile Ala Lys Ile Ala Gly Lys Ile
15                            20
Ala
```

( 2 ) INFORMATION FOR SEQ ID NO:60:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:60:

```
Lys Ile Ala Gly Lys Ile Ala Lys Ile Ala
5                             10
Gly Lys Ile Ala Lys Ile Ala Gly Ala Ile
15                            20
Ala
```

( 2 ) INFORMATION FOR SEQ ID NO:61:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:61:

```
Lys Leu Ala Ser Lys Ala Ala Lys Ile Ala
5                             10
Ala Lys Ile Ala Lys Val Ala Leu Lys Ala
15                            20
Leu
```

( 2 ) INFORMATION FOR SEQ ID NO:62:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:62:

```
Lys Ile Ala Lys Lys Ile Ala Lys Ile Ala
5                             10
Lys Lys Ile Ala Lys Ile Ala Lys Lys Ile
15                            20
Ala
```

( 2 ) INFORMATION FOR SEQ ID NO:63:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:63:

Lys Phe Ala Lys Lys Phe Ala Lys Phe Ala
                  5                  10
Lys Lys Phe Ala Lys Phe Ala Lys Lys Phe
                 15                  20
Ala ( 2 ) INFORMATION FOR SEQ ID NO:64:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:64:

Lys Phe Ala Lys Lys Ile Ala Lys Phe Ala
                  5                  10
Lys Lys Ile Ala Lys Phe Ala Lys Lys Ile
                 15                  20
Ala ( 2 ) INFORMATION FOR SEQ ID NO:65:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:65:

Ala Ile Ala Gly Lys Ile Ala Lys Ile Ala
                  5                  10
Gly Lys Ile Ala Lys Ile Ala Gly Lys Ile
                 15                  20
Ala ( 2 ) INFORMATION FOR SEQ ID NO:66:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:66:

Lys Ile Ala Gly Lys Ile Ala Ala Ile Ala
                  5                  10
Gly Lys Ile Ala Lys Ile Ala Gly Lys Ile
                 15                  20
Ala ( 2 ) INFORMATION FOR SEQ ID NO:67:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( D ) OTHER INFORMATION: amide- terminated ( x i ) SEQUENCE DESCRIPTION: SEQ ID NO:67:

```
Lys Ile Ala Gly Lys Ile Ala Lys Ile Ala
 5                      10
Gly Lys Ile Ala Ala Ile Ala Gly Lys Ile
15                      20
Ala
```

( 2 ) INFORMATION FOR SEQ ID NO:68:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: amide- terminated ( x i ) SEQUENCE DESCRIPTION: SEQ ID NO:68:

```
Gly Met Ala Ser Lys Ala Gly Lys Ile Ala
 5                      10
Gly Lys Ile Ala Lys Val Ala Leu Lys Ala
15                      20
Leu
```

( 2 ) INFORMATION FOR SEQ ID NO:69:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Magainin I peptide.
        ( D ) OTHER INFORMATION: amide- or carboxy- terminated ( x ) PUBLICATION INFORMATION:
        ( A ) AUTHORS: Zasloff, Michael
        ( C ) JOURNAL: Proc. Nat. Acad. Sci.
        ( D ) VOLUME: 84
        ( F ) PAGES: 5449-5453
        ( G ) DATE: AUG - 1987
        ( H ) DOCUMENT NUMBER: US 4810777
        ( I ) FILING DATE: 04-MAR-1987
        ( J ) PUBLICATION DATE: 07-MAR- 1989

( x i ) SEQUENCE DESCRIPTION: SEQ ID NO:69:

```
Gly Ile Gly Lys Phe Leu His Ser Ala Gly
 5                      10
Lys Phe Gly Lys Ala Phe Val Gly Glu Ile
15                      20
Met Lys Ser
```

( 2 ) INFORMATION FOR SEQ ID NO:70:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Magainin II peptide.
        ( D ) OTHER INFORMATION: amide- or carboxy- terminated ( x ) PUBLICATION INFORMATION:

(A) AUTHORS: Zasloff, Michael
(C) JOURNAL: Proc. Nat. Acad. Sci.
(D) VOLUME: 84
(F) PAGES: 5449-5453
(G) DATE: AUG - 1987
(H) DOCUMENT NUMBER: US 4810777
(I) FILING DATE: 04-MAR-1987
(J) PUBLICATION DATE: 07-MAR- 1989

(x i) SEQUENCE DESCRIPTION: SEQ ID NO:70:

Gly Ile Gly Lys Phe Leu His Ser Ala Lys
5                                     10
Lys Phe Gly Lys Ala Phe Val Gly Glu Ile
15                                    20
Met Asn Ser (2) INFORMATION FOR SEQ ID NO:71:

(i) SEQUENCE CHARACTERISTICS:
  (A) LENGTH: 22 amino acids
  (B) TYPE: amino acid
  (C) STRANDEDNESS:
  (D) TOPOLOGY: linear (i i) MOLECULE TYPE: peptide (i x) FEATURE:
  (A) NAME/KEY: Magainin III peptide.
  (D) OTHER INFORMATION: amide- or carboxy- terminated (x) PUBLICATION INFORMATION:
  (A) AUTHORS: Zasloff, Michael
  (C) JOURNAL: Proc. Nat. Acad. Sci.
  (D) VOLUME: 84
  (F) PAGES: 5449-5453
  (G) DATE: AUG - 1987
  (H) DOCUMENT NUMBER: US 4810777
  (I) FILING DATE: 04-MAR-1987
  (J) PUBLICATION DATE: 07-MAR- 1989

(x i) SEQUENCE DESCRIPTION: SEQ ID NO:71:

Gly Ile Gly Lys Phe Leu His Ser Ala Lys
5                                     10
Lys Phe Gly Lys Ala Phe Val Gly Glu Ile
15                                    20
Met Asn (2) INFORMATION FOR SEQ ID NO:72:

(i) SEQUENCE CHARACTERISTICS:
  (A) LENGTH: 22 amino acids
  (B) TYPE: amino acid
  (C) STRANDEDNESS:
  (D) TOPOLOGY: linear (i i) MOLECULE TYPE: peptide (i x) FEATURE:
  (A) NAME/KEY: magainin peptide.
  (D) OTHER INFORMATION: amide- or carboxy- terminated (x) PUBLICATION INFORMATION:
  (A) AUTHORS: Zasloff, Michael
  (C) JOURNAL: Proc. Nat. Acad. Sci.
  (D) VOLUME: 84
  (F) PAGES: 5449-5453
  (G) DATE: AUG - 1987
  (H) DOCUMENT NUMBER: US 4810777
  (I) FILING DATE: 04-MAR-1987
  (J) PUBLICATION DATE: 07-MAR- 1989

(x i) SEQUENCE DESCRIPTION: SEQ ID NO:72:

Ile Gly Lys Phe Leu His Ser Ala Lys Lys
5                                     10
Phe Gly Lys Ala Phe Val Gly Glu Ile Met
15                                    20
Asn Ser (2) INFORMATION FOR SEQ ID NO:73:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: magainin peptide.
    ( D ) OTHER INFORMATION: amide- or carboxy- terminated ( x ) PUBLICATION INFORMATION:
    ( A ) AUTHORS: Zasloff, Michael
    ( C ) JOURNAL: Proc. Nat. Acad. Sci.
    ( D ) VOLUME: 84
    ( F ) PAGES: 5449-5453
    ( G ) DATE: AUG - 1987
    ( H ) DOCUMENT NUMBER: US 4810777
    ( I ) FILING DATE: 04-MAR-1987
    ( J ) PUBLICATION DATE: 07-MAR- 1989

( x i ) SEQUENCE DESCRIPTION: SEQ ID NO:73:
```
Gly  Lys  Phe  Leu  His  Ser  Ala  Lys  Lys  Phe
 5                        10
Gly  Lys  Ala  Phe  Val  Gly  Glu  Ile  Met  Asn
15                        20
Ser
```

( 2 ) INFORMATION FOR SEQ ID NO:74:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: magainin peptide.
    ( D ) OTHER INFORMATION: amide- or carboxy- terminated ( x ) PUBLICATION INFORMATION:
    ( A ) AUTHORS: Zasloff, Michael
    ( C ) JOURNAL: Proc. Nat. Acad. Sci.
    ( D ) VOLUME: 84
    ( F ) PAGES: 5449-5453
    ( G ) DATE: AUG - 1987
    ( H ) DOCUMENT NUMBER: US 4810777
    ( I ) FILING DATE: 04-MAR-1987
    ( J ) PUBLICATION DATE: 07-MAR- 1989

( x i ) SEQUENCE DESCRIPTION: SEQ ID NO:74:
```
Lys  Phe  Leu  His  Ser  Ala  Lys  Lys  Phe  Gly
 5                        10
Lys  Ala  Phe  Val  Gly  Glu  Ile  Met  Asn  Ser
15                        20
```

( 2 ) INFORMATION FOR SEQ ID NO:75:

( i ) SEQUENCE CHARACTERISTICS:
    ( A ) LENGTH: 21 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: PGLa peptide.
    ( D ) OTHER INFORMATION: amide- terminated ( x ) PUBLICATION INFORMATION:
    ( A ) AUTHORS: Hoffman, et al.
    ( C ) JOURNAL: EMBO J.
    ( D ) VOLUME: 2
    ( F ) PAGES: 711-714

(G) DATE: 1983
(A) AUTHORS: Andreu, et al.
(C) JOURNAL: Journal of Biochemistry
(D) VOLUME: 149
(F) PAGES: 531-535
(G) DATE: 1985
(A) AUTHORS: Gibson, et al.
(C) JOURNAL: J. Biol. Chem.
(D) VOLUME: 261
(F) PAGES: 5341-5349
(G) DATE: 1986
(A) AUTHORS: Giovannini, et al.
(C) JOURNAL: Biochem J.
(D) VOLUME: 243
(F) PAGES: 113-120
(G) DATE: 1987

(x i) SEQUENCE DESCRIPTION: SEQ ID NO:75:

```
Gly Met Ala Ser Lys Ala Gly Ala Ile Ala
 5                                    10
Gly Lys Ile Ala Lys Val Ala Leu Lys Ala
15                                    20
Leu
```

(2) INFORMATION FOR SEQ ID NO:76:

(i) SEQUENCE CHARACTERISTICS:
      (A) LENGTH: 25 amino acids
      (B) TYPE: amino acid
      (C) STRANDEDNESS:
      (D) TOPOLOGY: linear (ii) MOLECULE TYPE: peptide (ix) FEATURE:
      (A) NAME/KEY: XPF peptide.

(x) PUBLICATION INFORMATION:
      (A) AUTHORS: Hoffman, et al.
      (C) JOURNAL: EMBO J.
      (D) VOLUME: 2
      (F) PAGES: 711-714
      (G) DATE: 1983
      (A) AUTHORS: Andreu, et al.
      (C) JOURNAL: Journal of Biochemistry
      (D) VOLUME: 149
      (F) PAGES: 531-535
      (G) DATE: 1985
      (A) AUTHORS: Gibson, et al.
      (C) JOURNAL: J. Biol. Chem.
      (D) VOLUME: 261
      (F) PAGES: 5341-5349
      (G) DATE: 1986
      (A) AUTHORS: Giovannini, et al.
      (C) JOURNAL: Biochem J.
      (D) VOLUME: 243
      (F) PAGES: 113-120
      (G) DATE: 1987

(x i) SEQUENCE DESCRIPTION: SEQ ID NO:76:

```
Gly Trp Ala Ser Lys Ile Gly Gln Thr Leu
 5                                    10
Gly Lys Ile Ala Lys Val Gly Leu Lys Glu
15                                    20
Leu Ile Gln Pro Lys
25
```

(2) INFORMATION FOR SEQ ID NO:77:

(i) SEQUENCE CHARACTERISTICS:
      (A) LENGTH: 27 amino acids
      (B) TYPE: amino acid
      (D) TOPOLOGY: linear (ii) MOLECULE TYPE: peptide (ix) FEATURE:
      (A) NAME/KEY: CPF peptide.
      (D) OTHER INFORMATION: amide- or carboxy- terminated (x) PUBLICATION INFORMATION:
  (A) AUTHORS: Richter, K.
        Egger, R.
        Kreil
  (C) JOURNAL: J. Biol. Chem.
  (D) VOLUME: 261
  (F) PAGES: 3676-3680
  (G) DATE: 1986
  (A) AUTHORS: Wakabayashi, T.
        Kato, H.
        Tachibaba, S.
  (C) JOURNAL: Nucleic Acids Research
  (D) VOLUME: 13
  (F) PAGES: 1817-1828
  (G) DATE: 1985
  (A) AUTHORS: Gibson, B.W.
        Poulter, L.
        Williams, D.H.
        Maggio, J.E.
  (C) JOURNAL: J. Biol. Chem.
  (D) VOLUME: 261
  (F) PAGES: 5341-5349
  (G) DATE: 1986
  (H) DOCUMENT NUMBER: WO90/04407
  (I) FILING DATE: 16-OCT-1989
  (J) PUBLICATION DATE: 03-MAY-1990

(xi) SEQUENCE DESCRIPTION: SEQ ID NO:77:

```
Gly  Phe  Gly  Ser  Phe  Leu  Gly  Leu  Ala  Leu
 5                          10
Lys  Ala  Ala  Leu  Lys  Ile  Gly  Ala  Asn  Ala
15                          20
Leu  Gly  Gly  Ala  Pro  Gln  Gln
25
```

(2) INFORMATION FOR SEQ ID NO:78:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: CPF peptide.
        (D) OTHER INFORMATION: amide- or carboxy- terminated (x) PUBLICATION INFORMATION:
        (A) AUTHORS: Richter, K
              Egger, R.
              Kreil
        (C) JOURNAL: J. Biol. Chem.
        (D) VOLUME: 261
        (F) PAGES: 3676-3680
        (G) DATE: 1986
        (A) AUTHORS: Wakabayashi, T.
              Kato, H.
              Tachibaba, S.
        (C) JOURNAL: Nucleic Acids Research
        (D) VOLUME: 13
        (F) PAGES: 1817-1828
        (G) DATE: 1985
        (A) AUTHORS: Gibson, B.W.
              Poulter, L.
              Williams, D.H.
              Maggio, J.E.
        (C) JOURNAL: J. Biol. Chem.
        (D) VOLUME: 261
        (F) PAGES: 5341-5349
        (G) DATE: 1986
        (H) DOCUMENT NUMBER: WO90/04407
        (I) FILING DATE: 16-OCT-1989
        (J) PUBLICATION DATE: 03-MAY-1990

(xi) SEQUENCE DESCRIPTION: SEQ ID NO:78:

```
Gly  Leu  Ala  Ser  Phe  Leu  Gly  Lys  Ala  Leu
```

```
                       5                          1 0
                 Lys  Ala  Gly  Leu  Lys  Ile  Gly  Ala  His  Leu
                 1 5                          2 0
                 Leu  Gly  Gly  Ala  Pro  Gln  Gln
                 2 5
```

( 2 ) INFORMATION FOR SEQ ID NO:79:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.
        ( D ) OTHER INFORMATION: amide- or carboxy- terminated ( x ) PUBLICATION INFORMATION:
        ( A ) AUTHORS: Richter, K.
            Egger, R.
            Kreil
        ( C ) JOURNAL: J. Biol. Chem.
        ( D ) VOLUME: 261
        ( F ) PAGES: 3676-3680
        ( G ) DATE: 1986
        ( A ) AUTHORS: Wakabayashi, T.
            Kato, H.
            Tachibaba, S.
        ( C ) JOURNAL: Nucleic Acids Research
        ( D ) VOLUME: 13
        ( F ) PAGES: 1817-1828
        ( G ) DATE: 1985
        ( A ) AUTHORS: Gibson, B.W.
            Poulter, L.
            Williams, D.H.
            Maggio, J.E.
        ( C ) JOURNAL: J. Biol. Chem.
        ( D ) VOLUME: 261
        ( F ) PAGES: 5341-5349
        ( G ) DATE: 1986
        ( H ) DOCUMENT NUMBER: WO90/04407
        ( I ) FILING DATE: 16-OCT-1989
        ( J ) PUBLICATION DATE: 03-MAY-1990

( x i ) SEQUENCE DESCRIPTION: SEQ ID NO:79:

```
                 Gly  Leu  Ala  Ser  Leu  Leu  Gly  Lys  Ala  Leu
                 5                          1 0
                 Lys  Ala  Gly  Leu  Lys  Ile  Gly  Thr  His  Phe
                 1 5                          2 0
                 Leu  Gly  Gly  Ala  Pro  Gln  Gln
                 2 5
```

( 2 ) INFORMATION FOR SEQ ID NO:80:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: CPF peptide.
        ( D ) OTHER INFORMATION: amide- or carboxy- terminated ( x ) PUBLICATION INFORMATION:
        ( A ) AUTHORS: Richter, K.
            Egger, R.
            Kreil
        ( C ) JOURNAL: J. Biol. Chem.
        ( D ) VOLUME: 261
        ( F ) PAGES: 3676-3680
        ( G ) DATE: 1986
        ( A ) AUTHORS: Wakabayashi, T.
            Kato, H.

Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:80:

```
Gly Leu Ala Ser Leu Leu Gly Lys Ala Leu
 5                        10
Lys Ala Thr Leu Lys Ile Gly Thr His Phe
15                        20
Leu Gly Gly Ala Pro Gln Gln
25
```

(2) INFORMATION FOR SEQ ID NO:81:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.
(D) OTHER INFORMATION: amide- or carboxy- terminated (x) PUBLICATION INFORMATION:
(A) AUTHORS: Richter, K.
Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:81:

```
Gly Phe Ala Ser Phe Leu Gly Lys Ala Leu
 5                        10
Lys Ala Ala Leu Lys Ile Gly Ala Asn Met
15                        20
Leu Gly Gly Thr Pro Gln Gln
25
```

(2) INFORMATION FOR SEQ ID NO:82:

(i) SEQUENCE CHARACTERISTICS:
(A) LENGTH: 27 amino acids
(B) TYPE: amino acid (C) STRANDEDNESS:
(D) TOPOLOGY: linear (i i) MOLECULE TYPE: peptide (i x) FEATURE:
    (A) NAME/KEY: CPF peptide.
    (D) OTHER INFORMATION: amide- or carboxy- terminated (x) PUBLICATION INFORMATION:
    (A) AUTHORS: Richter, K.
          Egger, R.
          Kreil
    (C) JOURNAL: J. Biol. Chem.
    (D) VOLUME: 261
    (F) PAGES: 3676-3680
    (G) DATE: 1986
    (A) AUTHORS: Wakabayashi, T.
          Kato, H.
          Tachibaba, S.
    (C) JOURNAL: Nucleic Acids Research
    (D) VOLUME: 13
    (F) PAGES: 1817-1828
    (G) DATE: 1985
    (A) AUTHORS: Gibson, B.W.
          Poulter, L.
          Williams, D.H.
          Maggio, J.E.
    (C) JOURNAL: J. Biol. Chem.
    (D) VOLUME: 261
    (F) PAGES: 5341-5349
    (G) DATE: 1986
    (H) DOCUMENT NUMBER: WO90/04407
    (I) FILING DATE: 16-OCT-1989
    (J) PUBLICATION DATE: 03-MAY-1990

(x i) SEQUENCE DESCRIPTION: SEQ ID NO:82:

```
Gly Phe Gly Ser Phe Leu Gly Lys Ala Leu
 5                          10
Lys Ala Ala Leu Lys Ile Gly Ala Asn Ala
15                          20
Leu Gly Gly Ala Pro Gln Gln
25
```

(2) INFORMATION FOR SEQ ID NO:83:

(i) SEQUENCE CHARACTERISTICS:
        (A) LENGTH: 27 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: CPF peptide.
        (D) OTHER INFORMATION: amide- or carboxy- terminated (x) PUBLICATION INFORMATION:
        (A) AUTHORS: Richter, K.
            Egger, R.
            Kreil
        (C) JOURNAL: J. Biol. Chem.
        (D) VOLUME: 261
        (F) PAGES: 3676-3680
        (G) DATE: 1986
        (A) AUTHORS: Wakabayashi, T.
            Kato, H.
            Tachibaba, S.
        (C) JOURNAL: Nucleic Acids Research
        (D) VOLUME: 13
        (F) PAGES: 1817-1828
        (G) DATE: 1985
        (A) AUTHORS: Gibson, B.W.
            Poulter, L.
            Williams, D.H.
            Maggio, J.E.
        (C) JOURNAL: J. Biol. Chem.
        (D) VOLUME: 261

(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:83:

Gly Phe Gly Ser Phe Leu Gly Lys Ala Leu
5                         10
Lys Ala Ala Leu Lys Ile Gly Ala Asn Ala
15                        20
Leu Gly Gly Ser Pro Gln Gln
25

(2) INFORMATION FOR SEQ ID NO:84:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.
(D) OTHER INFORMATION: amide- or carboxy- terminated (x) PUBLICATION INFORMATION:
(A) AUTHORS: Richter, K.
        Egger, R.
        Kreil
(C) JOURNAL: J. Biol. Chem.
(D) VOLUME: 261
(F) PAGES: 3676-3680
(G) DATE: 1986
(A) AUTHORS: Wakabayashi, T.
        Kato, H.
        Tachibaba, S.
(C) JOURNAL: Nucleic Acids Research
(D) VOLUME: 13
(F) PAGES: 1817-1828
(G) DATE: 1985
(A) AUTHORS: Gibson, B.W.
        Poulter, L.
        Williams, D.H.
        Maggio, J.E.
(C) JOURNAL: J. Biol. Chem.
(D) VOLUME: 261
(F) PAGES: 5341-5349
(G) DATE: 1986
(H) DOCUMENT NUMBER: WO90/04407
(I) FILING DATE: 16-OCT-1989
(J) PUBLICATION DATE: 03-MAY-1990

(xi) SEQUENCE DESCRIPTION: SEQ ID NO:84:

Gly Phe Ala Ser Phe Leu Gly Lys Ala Leu
5                         10
Lys Ala Ala Leu Lys Ile Gly Ala Asn Leu
15                        20
Leu Gly Gly Thr Pro Gln Gln
25

(2) INFORMATION FOR SEQ ID NO:85:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.
(D) OTHER INFORMATION: amide- or carboxy- terminated (x) PUBLICATION INFORMATION:
(A) AUTHORS: Richter, K.

Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986

(xi) SEQUENCE DESCRIPTION: SEQ ID NO:85:

Gly Phe Ala Ser Phe Leu Gly Lys Ala Leu
5                                    10
Lys Ala Ala Leu Lys Ile Gly Ala Asn Ala
15                                   20
Leu Gly Gly Ala Pro Gln Gln
25

(2) INFORMATION FOR SEQ ID NO:86:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.
(D) OTHER INFORMATION: amide- or carboxy- terminated (x) PUBLICATION INFORMATION:
(A) AUTHORS: Richter, K.
Egger, R.
Kreil
(C) JOURNAL: J. Biol. Chem.
(D) VOLUME: 261
(F) PAGES: 3676-3680
(G) DATE: 1986
(A) AUTHORS: Wakabayashi, T.
Kato, H.
Tachibaba, S.
(C) JOURNAL: Nucleic Acids Research
(D) VOLUME: 13
(F) PAGES: 1817-1828
(G) DATE: 1985
(A) AUTHORS: Gibson, B.W.
Poulter, L.
Williams, D.H.
Maggio, J.E.
(C) JOURNAL: J. Biol. Chem.
(D) VOLUME: 261
(F) PAGES: 5341-5349
(G) DATE: 1986

(xi) SEQUENCE DESCRIPTION: SEQ ID NO:86:

Gly Phe Ala Ser Phe Leu Gly Lys Ala Leu
5                                    10
Lys Ala Ala Leu Lys Ile Gly Ala Asn Met
15                                   20
Leu Gly Gly Ala Pro Gln Gln
25

(2) INFORMATION FOR SEQ ID NO:87:

(i) SEQUENCE CHARACTERISTICS:

(A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: CPF peptide.
        (D) OTHER INFORMATION: amide- or carboxy- terminated (x) PUBLICATION INFORMATION:
        (A) AUTHORS: Richter, K.
                Egger, R.
                Kreil
        (C) JOURNAL: J. Biol. Chem.
        (D) VOLUME: 261
        (F) PAGES: 3676-3680
        (G) DATE: 1986
        (A) AUTHORS: Wakabayashi, T.
                Kato, H.
                Tachibaba, S.
        (C) JOURNAL: Nucleic Acids Research
        (D) VOLUME: 13
        (F) PAGES: 1817-1828
        (G) DATE: 1985
        (A) AUTHORS: Gibson, B.W.
                Poulter, L.
                Williams, D.H.
                Maggio, J.E.
        (C) JOURNAL: J. Biol. Chem.
        (D) VOLUME: 261
        (F) PAGES: 5341-5349
        (G) DATE: 1986

(xi) SEQUENCE DESCRIPTION: SEQ ID NO:87:
        Gly  Phe  Gly  Ser  Phe  Leu  Gly  Lys  Ala  Leu
        5                             10
        Lys  Ala  Ala  Leu  Lys  Ile  Gly  Ala  Asn  Ala
        15                            20
        Leu  Gly  Gly  Ser  Leu  Gln  Gln
        25

(2) INFORMATION FOR SEQ ID NO:88:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: CPF peptide.
        (D) OTHER INFORMATION: amide- or carboxy- terminated (x) PUBLICATION INFORMATION:
        (A) AUTHORS: Richter, K.
                Egger, R.
                Kreil
        (C) JOURNAL: J. Biol. Chem.
        (D) VOLUME: 261
        (F) PAGES: 3676-3680
        (G) DATE: 1986
        (A) AUTHORS: Wakabayashi, T.
                Kato, H.
                Tachibaba, S.
        (C) JOURNAL: Nucleic Acids Research
        (D) VOLUME: 13
        (F) PAGES: 1817-1828
        (G) DATE: 1985
        (A) AUTHORS: Gibson, B.W.
                Poulter, L.
                Williams, D.H.
                Maggio, J.E.
        (C) JOURNAL: J. Biol. Chem.
        (D) VOLUME: 261
        (F) PAGES: 5341-5349

(G) DATE: 1986

(x i) SEQUENCE DESCRIPTION: SEQ ID NO:88:

```
Gly Phe Gly Ser Phe Leu Gly Lys Ala Leu
5                        10
Lys Ala Gly Leu Lys Ile Gly Thr Asn Phe
15                       20
Leu Gly Gly Ala Pro Gln Gln
25
```

(2) INFORMATION FOR SEQ ID NO:89:

(i) SEQUENCE CHARACTERISTICS:
(A) LENGTH: 27 amino acids
(B) TYPE: amino acid
(C) STRANDEDNESS:
(D) TOPOLOGY: linear (ii) MOLECULE TYPE: peptide (ix) FEATURE:
(A) NAME/KEY: CPF peptide.
(D) OTHER INFORMATION: amide- or carboxy- terminated (x) PUBLICATION INFORMATION:
(A) AUTHORS: Richter, K
        Egger, R.
        Kreil
(C) JOURNAL: J. Biol. Chem.
(D) VOLUME: 261
(F) PAGES: 3676-3680
(G) DATE: 1986
(A) AUTHORS: Wakabayashi, T.
        Kato, H.
        Tachibaba, S.
(C) JOURNAL: Nucleic Acids Research
(D) VOLUME: 13
(F) PAGES: 1817-1828
(G) DATE: 1985
(A) AUTHORS: Gibson, B.W.
        Poulter, L.
        Williams, D.H.
        Maggio, J.E.
(C) JOURNAL: J. Biol. Chem.
(D) VOLUME: 261
(F) PAGES: 5341-5349
(G) DATE: 1986

(x i) SEQUENCE DESCRIPTION: SEQ ID NO:89:

```
Gly Leu Ala Ser Leu Leu Gly Lys Ala Leu
5                        10
Lys Ala Ala Leu Lys Ile Gly Ala Asn Ala
15                       20
Leu Gly Gly Ser Pro Gln Gln
25
```

PEPTIDE COMPOSITIONS AND USES THEREFOR

This application is a continuation-in-part of application Ser. No. 686,115, filed Apr. 15, 1991 now abandoned, which is a continuation in part of application Ser. No. 476,629, filed Feb. 8, 1990, now abandoned.

This invention relates to biologically active peptides, and more particularly to novel biologically active peptides and uses therefor.

In accordance with an aspect of the present invention, there is provided a biologically active amphiphilic peptide which includes the following structural formula $X_a$: $R_1$—$R_2$—$R_2$—$R_1$—$R_2$—$R_2$—$R_3$—$R_1$—$R_2$—$R_2$—$R_1$—$R_2$—$R_2$—$R_3$—$R_1$—$R_2$—$R_2$, wherein $R_1$ is a basic hydrophilic amino acid, $R_2$ is a hydrophobic amino acid, and $R_3$ is a neutral hydrophilic or hydrophobic amino acid.

In one embodiment, the peptide has the structure $Y_a$—$X_a$, wherein $X_a$ is as hereinabove described and $Y_a$ is:
(i) $R_2$;
(ii) $R_2$—$R_2$; or
(iii) $R_2$—$R_2$—$R_2$.

In accordance with another aspect of the present invention, there is provided a biologically active amphiphilic peptide which includes the following structural formula $X_b$: $R_1$—$R_2$—$R_2$—$R_3$—$R_1$—$R_2$—$R_2$—$R_1$—$R_2$—$R_2$—$R_3$—$R_1$—$R_2$—$R_2$—$R_2$, wherein $R_1$, $R_2$, and $R_3$ are as hereinabove described.

In one embodiment, the peptide has the structure $X_b$—$Z_b$, wherein $X_b$ is the peptide structure hereinabove described and $Z_b$ is:
(i) $R_2$;
(ii) $R_2$—$R_1$; or
(iii) $R_2$—$R_1$—$R_2$.

In accordance with another aspect of the present invention, there is provided a biologically active amphiphilic peptide which includes one of the following basic structures $X_1$ through $X_7$ wherein:

$X_1$ is —[$R_1$—$R_2$—$R_2$—$R_3$—$R_1$—$R_2$—$R_2$]—$_n$;
$X_2$ is —[$R_2$—$R_2$—$R_3$—$R_1$—$R_2$—$R_2$—$R_1$]—$_n$;
$X_3$ is —[$R_2$—$R_3$—$R_1$—$R_2$—$R_2$—$R_1$—$R_2$]—$_n$;
$X_4$ is —[$R_3$—$R_1$—$R_2$—$R_2$—$R_1$—$R_2$—$R_2$]—$_n$;
$X_5$ is —[$R_1$—$R_2$—$R_2$—$R_1$—$R_2$—$R_2$—$R_3$]—$_n$;
$X_6$ is —[$R_2$—$R_2$—$R_1$—$R_2$—$R_2$—$R_3$—$R_1$]—$_n$; and
$X_7$ is —[$R_2$—$R_1$—$R_2$—$R_2$—$R_3$—$R_1$—$R_2$]—$_n$;

wherein $R_1$ is a basic hydrophilic amino acid, $R_2$ is a hydrophobic amino acid, $R_3$ is a neutral hydrophilic or hydrophobic amino acid, and n is from 3 to 5.

The basic hydrophilic amino acids include, but are not limited to Lys, Arg, His, Orn, homoarginine (Har), 2, 4-diamino butyric acid (Dbu), and p-aminophenylalanine.

The hydrophobic amino acids include, but are not limited to Ala, Cys, Phe, Gly, Ile, Leu, Met, Pro, Val, Trp, Tyr, norleucine (Nle), norvaline (Nva), and cyclohexylalanine (Cha).

The neutral hydrophilic amino acids include, but are not limited to Asn, Gln, Ser and Thr.

In accordance with one embodiment, when the peptide includes the structure X1, the peptide may include the following structure:
$Y_1$—$X_1$, wherein $X_1$ is as hereinabove described, and Y is:
(i) $R_2$;
(ii) $R_2$—$R_2$;
(iii) $R_1$—$R_2$—$R_2$;
(iv) $R_3$—$R_1$—$R_2$—$R_2$;
(v) $R_2$—$R_3$—$R_1$—$R_2$—$R_2$; or
(vi) $R_2$—$R_2$—$R_3$—$R_1$—$R_2$—$R_2$, wherein $R_1$, $R_2$, and $R_3$ are as hereinabove described In accordance with another embodiment, when the peptide includes the structure $X_1$, the peptide may include the following structure:
$x_1$—$y_1$, wherein $x_1$ is as hereinabove described, and $y_1$ is:
(i) $R_1$;
(ii) $R_1$—$R_2$;
(iii) $R_1$—$R_2$—$R_2$;
(iv) $R_1$—$R_2$—$R_2$—$R_3$;
(v) $R_1$—$R_2$—$R_2$—$R_3$—$R_1$; or
(vi) $R_1$—$R_2$—$R_2$—$R_3$—$R_1$—$R_2$.

In accordance with yet another embodiment, the peptide may include the following structure:
$(Y_1)_a$—$X_1$—$(Z_1)_b$, wherein $Y_1$ and $Z_1$ are as previously defined, a is 0 or 1, and b is 0 or 1.

When the peptide includes the structure $X_2$, the peptide may include the following structure:
$Y_2$—$X_2$, wherein $X_2$ is as hereinabove described, and $Y_2$ is:
(i) $R_1$;
(ii) $R_2$—$R_1$;
(iii) $R_2$—$R_2$—$R_1$;
(iv) $R_1$—$R_2$—$R_2$—$R_1$;
(v) $R_3$—$R_1$—$R_2$—$R_2$—$R_1$; or
(vi) $R_2$—$R_3$—$R_1$—$R_2$—$R_2$—$R_1$.

In another embodiment, the peptide may include the following structure: $X_2$ - $Z_2$ wherein $X_2$ is as hereinabove described, and $Z_2$ is:
(i) $R_2$;
(ii) $R_2$—$R_2$;
(iii) $R_2$—$R_2$—$R_3$;
(iv) $R_2$—$R_2$—$R_3$—$R_1$;
(v) $R_2$—$R_2$—$R_3$—$R_1$—$R_2$; or
(vi) $R_2$—$R_2$—$R_3$—$R_1$—$R_2$—$R_2$.

In accordance with yet another embodiment, the peptide may include the following structure:
$(Y_2)_a$—$X_2$—$(Z_2)_b$, wherein $Y_2$ and $Z_2$ are as previously defined, a is 0 or 1, and b is 0 or 1.

In accordance with another embodiment, when the peptide includes the structure $X_3$, the peptide may include the following structure:
$Y_3$—$X_3$ wherein $X_3$ is as hereinabove described, and $Y_3$ is:
(i) $R_2$;
(ii) $R_1$—$R_2$;
(iii) $R_2$—$R_1$—$R_2$;
(iv) $R_2$—$R_2$—$R_1$—$R_2$;
(v) $R_1$—$R_2$—$R_2$—$R_1$—$R_2$; or
(vi) $R_3$—$R_1$—$R_2$—$R_2$—$R_1$—$R_2$, wherein $R_1$, $R_2$, and $R_3$ are as hereinabove described.

In accordance with another embodiment, when the peptide includes the structure $X_3$, the peptide may include the following structure:
$X_3$—$Z_3$ wherein $X_3$ is as hereinabove described, and $Z_3$ is:
(i) $R_2$;
(ii) $R_2$—$R_3$;
(iii) $R_2$—$R_3$—$R_1$;

(iv) $R_2$—$R_3$—$R_1$—$R_2$;
(v) $R_2$—$R_3$—$R_1$—$R_2$—$R_2$; or
(vi) $R_2$—$R_3$—$R_1$—$R_2$—$R_2$—$R_1$.

In accordance with yet another embodiment, the peptide may include the following structure:

$(Y_3)_a$—$X_3$—$(Z_3)_b$, wherein Y and Z are as previously defined, a is 0 or 1, and b is 0 or 1.

In accordance with yet another embodiment, when the peptide includes the structure $X_4$, the peptide may include the following structure:

$Y_4$—$X_4$, wherein $X_4$ is as hereinabove described, and $Y_4$ is:

(i) $R_2$;
(ii) $R_2$—$R_2$;
(iii) $R_1$—$R_2$—$R_2$;
(iv) $R_2$—$R_1$—$R_2$—$R_2$;
(v) $R_2$—$R_2$—$R_1$—$R_2$—$R_2$; or
(vi) $R_1$—$R_2$—$R_2$—$R_1$—$R_2$—$R_2$, wherein $R_1$, $R_2$ and $R_3$ are as hereinabove described.

In accordance with another embodiment, when the peptide includes the structure $X_4$, the peptide may include the following structure:

$X_4$—$Z_4$, wherein $X_4$ is as hereinabove described, and $Z_4$ is:

(i) $R_3$;
(ii) $R_3$—$R_1$;
(iii) $R_3$—$R_1$—$R_2$;
(iv) $R_3$—$R_1$—$R_2$—$R_2$;
(v) $R_3$—$R_1$—$R_2$—$R_2$—$R_1$; or
(vi) $R_3$—$R_1$—$R_2$—$R_2$—$R_1$—$R_2$.

In accordance with yet another embodiment, the peptide may include the following structure:

$(Y_4)_a$—$X_4(Z_4)_b$, wherein $X_4$ and $Z_4$ are as previously defined, a is 0 or 1, and b is 0 or 1.

In accordance with a further embodiment, when the peptide includes the structure $X_5$, the peptide may include the following structure:

$Y_5$—$X_5$, wherein $X_5$ is as hereinabove described, and $Y_5$ is:

(i) $R_3$;
(ii) $R_2$—$R_3$;
(iii) $R_2$—$R_2$—$R_3$;
(iv) $R_1$—$R_2$—$R_2$—$R_3$;
(v) $R_2$—$R_1$—$R_2$—$R_2$—$R_3$; or
(vi) $R_2$—$R_2$—$R_1$—$R_2$—$R_2$—$R_3$, wherein $R_1$, $R_2$ and $R_3$ are as hereinabove described.

In accordance with another embodiment, when the peptide includes structure $X_5$, the peptide may include the following structure:

$X_5$—$Z_5$ wherein $X_5$ is as hereinabove described, and $Z_5$ is:

(i) $R_1$;
(ii) $R_1$—$R_2$;
(iii) $R_1$—$R_2$—$R_2$;
(iv) $R_1$—$R_2$—$R_2$—$R_1$;
(v) $R_1$—$R_2$—$R_2$—$R_1$—$R_2$; or
(vi) $R_1$—$R_2$—$R_2$—$R_1$—$R_2$—$R_2$.

In accordance with yet another embodiment, the peptide may include the following structure:

$(Y_5)_a$—$X_5$ $(Z_5)_b$, wherein $X_5$ and $Z_5$ are as previously defined, a is 0 or 1, and b is 0 or 1.

In accordance with a further embodiment, when the peptide includes the structure $X_6$, the peptide may include the following structure:

$Y_6$—$X_6$ wherein $X_6$ is as hereinabove described, and $Y_6$ is:

(i) $R_1$;
(ii) $R_3$—$R_1$;
(iii) $R_2$—$R_3$—$R_1$;
(iv) $R_2$—$R_2$—$R_3$—$R_1$;
(v) $R_1$—$R_2$—$R_2$—$R_3$—$R_1$; or
(vi) $R_2$—$R_1$—$R_2$—$R_2$—$R_3$—$R_1$, wherein $R_1$, $R_2$, and $R_3$ are as hereinabove described.

In accordance with another embodiment, when the peptide includes the structure $X_6$, the peptide may include the following structure:

$X_6$—$Z_6$, wherein $X_6$ is as hereinabove described, and $Z_6$ is:

(i) $R_2$;
(ii) $R_2$—$R_2$;
(iii) $R_2$—$R_2$—$R_1$;
(iv) $R_2$—$R_2$—$R_1$—$R_2$;
(v) $R_2$—$R_2$—$R_1$—$R_2$—$R_2$; or
(vi) $R_2$—$R_2$—$R_1$—$R_2$—$R_2$—$R_3$.

In accordance with yet another embodiment, the peptide may include the following structure:

$(Y_6)_a$—$X_6$ $(Z6)_b$, wherein $Y_6$ and $Z_6$ are as previously defined, a is 0 or 1, and b is 0 or 1.

In accordance with one embodiment, when the peptide includes the structure $X_7$, the peptide may include the structure $Y_7$—$X_7$, wherein $X_7$ is as hereinabove described, and $Y_7$ is:

(i) $R_2$;
(ii) $R_1$—$R_2$;
(iii) $R_3$—$R_1$—$R_2$;
(iv) $R_2$—$R_3$—$R_1$—$R_2$;
(v) $R_2$—$R_2$—$R_3$—$R_1$—$R_2$; or
(vi) $R_1$—$R_2$—$R_2$—$R_3$—$R_1$—$R_2$, wherein $R_1$, $R_2$, and $R_3$ are as hereinabove described.

In accordance with a further embodiment, when the peptide includes the structure $X_7$, the peptide may include the following structure:

$X_7$—$Z_7$ wherein $X_7$ is as hereinabove described, and $Z_7$ is:

(i) $R_2$;
(ii) $R_2$—$R_1$;
(iii) $R_2$—$R_1$—$R_2$;
(iv) $R_2$—$R_1$—$R_2$—$R_2$;
(v) $R_2$—$R_1$—$R_2$—$R_2$—$R_3$; or
(vi) $R_2$—$R_1$—$R_2$—$R_2$—$R_3$—$R_1$.

In accordance with yet another embodiment, the peptide may include the following structure:

$(Y_7)_a$—$X_7$ $(Z_7)_b$, wherein $Y_7$ and $Z_7$ are as previously defined, a is 0 or 1, and b is 0 or 1.

The peptides and/or analogives or derivatives thereof, may be C-terminal acids or amides.

In a preferred embodiment, n is 3, and most preferably the peptide is of one of the following structures listed below and also listed in the accompanying sequence listing:

(Lys Ile Ala Gly Lys Ile Ala)$_3$—NH$_2$(SEQ ID NO: 1)
(Lys Ile Ala Lys Ile Ala Gly)$_3$—NH$_2$(SEQ ID NO: 2)
(Lys Ile Ala Gly Lys Ile Gly)$_3$—NH$_2$(SEQ ID NO: 3)
(Lys Leu Ala Gly Lys Leu Ala)$_3$—NH$_2$(SEQ ID NO: 4)
(Lys Phe Ala Gly Lys Phe Ala)$_3$—NH$_2$(SEQ ID NO: 5)

(Lys Ala Leu Ser Lys Ala Leu)$_3$—NH$_2$(SEQ ID NO: 6)
(Lys Leu Leu Lys Ala Leu Gly)$_3$—NH$_2$(SEQ ID NO: 7)
(Lys Ala Ile Gly Lys Ala Ile)$_3$—NH$_2$(SEQ ID NO: 8)
(Gly Ile Ala Lys Ile Ala Lys)$_3$—NH$_2$(SEQ ID NO: 9)
(Lys Ile Ala Lys Ile Phe Gly)$_3$—NH$_2$(SEQ ID NO: 10)
(Gly Ile Ala Arg Ile Ala Lys)$_3$—NH$_2$(SEQ ID NO: 11)
(Lys Phe Ala Arg Ile Ala Gly)$_3$—NH$_2$(SEQ ID NO: 12)
(Gly Phe Ala Lys Ile Ala Lys)$_3$—NH$_2$(SEQ ID NO: 13)
(Lys Ile Ala Gly Orn Ile Ala)$_3$—NH$_2$(SEQ ID NO: 14)
(Lys Ile Ala Arg Ile Ala Gly)$_3$—NH$_2$(SEQ ID NO: 15)
(Orn Ile Ala Gly Lys Ile Ala)$_3$—NH$_2$(SEQ ID NO: 16)
(Gly Ile Ala Arg Ile Phe Lys)$_3$—NH$_2$(SEQ ID NO: 17)
(Lys Nle Ala Gly Lys Nle Ala)$_3$—NH$_2$(SEQ ID NO: 18)
(Lys Nle Ala Gly Lys Ile Ala)$_3$—NH$_2$(SEQ ID NO: 19)
(Lys Ile Ala Gly Lys Nle Ala)$_3$—NH$_2$(SEQ ID NO: 20)
(Lys Nva Ala Gly Lys Nva Ala)$_3$—NH$_2$(SEQ ID NO: 21)
(Lys Nva Ala Gly Lys Ile Ala)$_3$—NH$_2$(SEQ ID NO: 22)
(Lys Leu Leu Ser Lys Leu Gly)$_3$—NH$_2$(SEQ ID NO: 23)
(Lys Leu Leu Ser Lys Phe Gly)$_3$—NH$_2$(SEQ ID NO: 24)
(Lys Ile Ala Gly Lys Nva Ala)$_3$—NH$_2$(SEQ ID NO: 25)
(His Ile Ala Gly His Ile Ala)$_3$—NH$_2$(SEQ ID NO: 26)
(Ala Gly Lys Ile Ala Lys Ile)$_3$—NH$_2$(SEQ ID NO: 27)
(Ile Ala Lys Ile Ala Gly Lys)$_3$—NH$_2$(SEQ ID NO: 28)
(Lys Ile Ala Gly Arg Ile Ala)$_3$—NH$_2$(SEQ ID NO: 29)
(Arg Ile Ala Gly Arg Ile Ala)$_3$—NH$_2$(SEQ ID NO: 30)
(Lys Val Ala Gly Lys Ile Ala)$_3$—NH$_2$(SEQ ID NO: 31)
(Lys Ile Ala Gly Lys Val Ala)$_3$—NH$_2$(SEQ ID NO: 32)
(Ala Lys Ile Ala Gly Lys Ile)$_3$—NH$_2$(SEQ ID NO: 33)
(Orn Ile Ala Gly Orn Ile Ala)$_3$—NH$_2$(SEQ ID NO: 34)
(Lys Phe Ala Gly Lys Ile Ala)$_3$—NH$_2$(SEQ ID NO: 35)
(Lys Ile Ala Gly Lys Phe Ala)$_3$—NH$_2$(SEQ ID NO: 36)
(Lys Cha Ala Gly Lys Ile Ala)$_3$—NH$_2$(SEQ ID NO: 37)
(Lys Nle Ala Lys Ile Ala Gly)$_3$—NH$_2$(SEQ ID NO: 38)
(Arg Ile Ala Gly Lys Ile Ala)$_3$—NH$_2$(SEQ ID NO: 39)
(Har Ile Ala Gly Har Ile Ala)$_3$—NH$_2$(SEQ ID NO: 40)
(Xaa Ile Ala Gly Lys Ile Ala)$_3$—NH$_2$(SEQ ID NO: 41)
(Lys Ile Ala Gly Xaa Ile Ala)$_3$—NH$_2$(SEQ ID NO: 42)
Lys Ile Ala (Lys Ile Ala Gly Lys Ile Ala)$_3$—NH$_2$ (SEQ ID NO:43)

In (SEQ ID NO:41) and (SEQ ID NO:42), Xaa is p-aminophenylalanine.

In accordance with another aspect of the present invention, there is provided a biologically active amphiphilic peptide which includes the following basic structure $X_{14}$:

$$R_1—R_2—R_2—R_3—R_4—R_2—R_1—R_2—R_2—R_2—R_4—R_2—R_2,$$

wherein $R_1$, $R_2$, and $R_3$ are as hereinabove described, and $R_4$ is a basic hydrophilic or hydrophobic amino acid.

In accordance with one embodiment, the peptide may include the following structure:

$Y_{14}—X_{14}$, wherein $X_{14}$ is as hereinabove described, and $Y_{14}$ is:

(i) $R_2$;
(ii) $R_2—R_2$;
(iii) $R_4—R_2—R_2$;
(iv) $R_3—R_4—R_2—R_2$;
(v) $R_2—R_3—R_4—R_2—R_2$;
(vi) $R_2—R_2—R_3—R_4—R_2—R_2$, or (vii) $R_1—R_2—R_2—R_3—R_4—R_2—R_2$, wherein $R_1$, $R_2$, $R_3$ and $R_4$ are as hereinabove described.

In accordance with another embodiment, the peptide may include the following structure:

$X_{14}—Z_{14}$, wherein $X_{14}$ is as hereinabove described and $Z_{14}$ is:

(i) $R_1$;
(ii) $R_1—R_2$;
(iii) $R_1—R_2—R_2$;
(iv) $R_1—R_2—R_2—R_3$;
(v) $R_1—R_2—R_2—R_3—R_4$;
(vi) $R_1—R_2—R_2—R_3—R_4—R_2$; or
(vii) $R_1—R_2—R_2—R_3—R_4—R_2—R_2$, wherein $R_1$, $R_2$, $R_3$, and $R_4$ are as hereinabove described.

In accordance with yet another embodiment the peptide may include the following structure:

$(Y_{14})_a—X_{14}—(Z_{14})_b$, wherein X and Y are as previously defined, a is 0 or 1, and b is 0 or 1. In a preferred embodiment, the peptide has the following structural formula as indicated in the accompanying sequence listing:

(SEQ ID NO: 44)—NH$_2$.

In another preferred embodiment, the peptide has the following structural formula as indicated in the accompanying sequence listing:

(SEQ ID NO: 45)—NH$_2$.

In accordance with a further embodiment, the peptide has one of the following structural formulae as indicated in the accompanying sequence listing:

(SEQ ID NO: 46)—NH$_2$
(SEQ ID NO: 47)—NH$_2$
(SEQ ID NO: 48)—NH$_2$
(SEQ ID NO: 49)—NH$_2$
(SEQ ID NO: 50)—NH$_2$
(SEQ ID NO: 51)—NH$_2$
(SEQ ID NO: 52)—NH$_2$
(SEQ ID NO: 53)—NH$_2$
(SEQ ID NO: 54)—NH$_2$
(SEQ ID NO: 55)—NH$_2$
(SEQ ID NO: 56)—NH$_2$
(SEQ ID NO: 57)—NH$_2$
(SEQ ID NO: 58)—NH$_2$
(SEQ ID NO: 59)—NH$_2$
(SEQ ID NO: 60)—NH$_2$
(SEQ ID NO: 61)—NH$_2$

In accordance with another aspect of the present invention, there is provided a biologically active amphiphilic peptide which includes the following structural formula:

—(Lys Ile Ala Lys Lys Ile Ala)—$_n$ wherein n is from 2 to 5. Preferably, n is 3, and the peptide has the following structural formula:

(Lys Ile Ala Lys Lys Ile Ala)$_3$—NH$_2$. (SEQ ID NO:62).

In accordance with another aspect of the present invention, there is provided a biologically active amphiphilic peptide which includes the following structural formula:

—(Lys Phe Ala Lys Lys Phe Ala)$_n$—, wherein n is from 2 to 5. Preferably, n is 3, and the peptide has the following structural formula:

(Lys Phe Ala Lys Lys Phe Ala)$_3$—NH$_2$ (SEQ ID NO:63).

In accordance with yet another aspect of the present invention, there is provided a biologically active amphiphilic peptide which includes the following structural formula:

—(Lys Phe Ala Lys Lys Ile Ala)$_n$—, wherein n is from 2 to 5. Preferably, n is 3, and the peptide has the following structural formula:

(Lys Phe Ala Lys Lys Ile Ala)$_3$—NH$_2$ (SEQ ID NO:64).

In accordance with another aspect of the present invention, there is provided a biologically active amphiphilic peptide selected from the group consisting of the following structural formulae as given in the accompanying sequence listing:

(SEQ ID NO: 65)—NH$_2$ (SEQ ID NO: 66)—NH$_2$ (SEQ ID NO: 67)—NH$_2$ (SEQ ID NO: 68)—NH$_2$

In accordance with one embodiment, each of the amino acid residues contained in the peptides is a D-amino acid residue or glycine. Although the scope of this particular embodiment is not to be limited to any theoretical reasoning, it is believed that the above-mentioned peptides, when consisting entirely of D-amino acid or glycine residues, may have increased resistance to proteolytic enzymes while retaining their biological activity. Such peptides thus may be administered orally. Thus in accordance with a preferred embodiment, all of the amino acid residues are either D-amino acid or glycine residues or L-amino acid or glycine residues.

An amphiphilic peptide is a peptide which includes both hydrophobic and hydrophilic peptide regions.

In general, the peptides hereinabove described, and/or analogues or derivatives thereof are generally water soluble to a concentration of at least 20 mg/ml at neutral pH in water. Such peptides are capable of forming an α-helical structure. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

In general, the peptides of the present invention are ion channel-forming peptides. An ion channel-forming peptide or ionophore is a peptide which increases the permeability for ions across a natural or synthetic lipid membrane. B. Christensen, et al., PNAS, Vol. 85, pgs. 5072–5076 (July 1988) describes methodology which indicates whether or not a peptide has ion channel-forming properties and is therefore an ionophore. As used herein an ion channel-forming peptide is a peptide which has ion channel-forming properties as determined by the method of Christensen, et al.

The peptides and/or analogues or derivatives thereof may be administered to a host; for example a human or non-human animal, in an amount effective to inhibit growth of a target cell, virus, or vitally-infected cell. Thus, for example, the peptides and/or analogues or derivatives thereof may be used as anti-microbial agents, anti-viral agents, antibiotics, anti-tumor agents, antiparasitic agents, antifungal agents, spermicides, as well as exhibiting other bioactive functions.

The term "antimicrobial" as used herein means that the peptides of the present invention inhibit, prevent, or destroy the growth or proliferation of microbes such as bacteria, fungi, or the like.

The term "antibiotic" as used herein means that the peptides employed in the present invention produce effects adverse to the normal biological functions of the non-host cell, tissue or organism, including death or destruction and prevention of the growth or proliferation of the non-host cell, tissue, or organism, when contacted with the peptides.

The term "spermicidal" as used herein means that the peptides employed in the present invention, inhibit, prevent, or destroy the motility of sperm.

The term "antiviral" as used herein means that the peptides employed in the present invention inhibit, prevent, or destroy the growth or proliferation of viruses, or of virally-infected cells.

The term anti-tumor as used herein means that the peptide inhibits the growth of or destroys tumors.

The term "antifungal" as used herein means that the peptides of the present invention may be used to inhibit the growth of or destroy fungi.

The term "antiparasitic" as used herein means that the peptides of the present invention may be used to inhibit the growth of or destroy parasites.

The peptides may be administered in vivo or in vitro. The peptides also may be administered directly to a target cell, virus, or virally-infected cell, or the peptides may be administered systemically.

The peptides of the present invention have a broad range of potent antibiotic activity against a plurality of microorganisms including Gram-positive and Gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic, antimicrobial, and antiviral properties of the peptides, they may also be used as preservatives or sterilants of materials susceptible to microbial or viral contamination.

The peptide and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptide(s) of the present invention may be administered to a host; in particular an animal, in an effective antibiotic and/or anti-tumor and/or anti-viral and/or anti-microbial and/or anti-parasitic and/or an antispermicidal amount.

Depending on the use, a composition in accordance with the invention will contain an effective anti-microbial amount and/or an effective antispermicidal amount and/or an effective anti-viral amount and/or an effective anti-tumor amount and/or an effective antibiotic amount and/or anti-parasitic amount of one or more of the hereinabove described peptides which have such activity.

The peptide of the present invention may also be employed in promoting or stimulating healing of a wound in a host.

The term "wound healing" as used herein includes various aspects of the would healing process.

These aspects include, but are not limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to reverse the inhibition of wound healing caused by steroids such as cortisone or by conditions which compromise or depress the immune system.

The peptides of the present invention may be used in the treatment of external burns and to treat and/or prevent skin and burn infections. In particular, the peptides may be used to treat skin and burn infections caused by organisms such as, but not limited to, *P. aeruginosa* and *S. aureus*.

The peptides are also useful in the prevention or treatment of eye infections. Such infections may be caused by bacteria such as, but not limited to, *P. aeruginosa, S. aureus,* and *N. gonorrhoeae,* by fungi such as but not limited to *C. albicans* and *A. fumigatus,* by parasites such as but not limited to *A. castellani,* or by viruses.

The peptides may also be effective in killing cysts, spores, or trophozoites of infection—causing organisms. Such organisms include, but are not limited to Acanthamoeba which forms trophozoites or cysts, *C. albicans,* which forms spores, and *A. fumigatus,* which forms spores as well.

The peptides may also be administered to plants in an effective antimicrobial or antiviral or antiparasitic amount to prevent or treat microbial or viral or parasitic contamination thereof.

In general, the peptide is employed to provide peptide dosages of from 0.1 mg. to 500 mg. per kilogram of host weight, when administered systemically. When administered topically, the peptide is used in a concentration of from 0.05% to 10%.

The peptides may be produced by known techniques and obtained in substantially pure form. For example, the peptides may be synthesized on an automatic peptide synthesizer. *Journal of the American Chemical Society,* Vol. 85, pgs. 2149–54 (1963). It is also possible to produce such peptides by genetic engineering techniques. The codons encoding the amino acids are known to those skilled in the art, and thus one may construct DNA encoding any of the peptides by accepted techniques, and clone such DNA into an expression vehicle such as, for example, a plasmid, and transfect such an expression vehicle into a cell which will express the peptide. Thus, it is contemplated within the scope of the present invention that one may administer the peptide to a host by administering to a host DNA encoding the peptides.

In accordance with another embodiment, the peptides of the present invention may be employed in combination with an ion having pharmacological properties for the purposes hereinabove described.

An ion having pharmacological properties is one which when introduced into a target cell, virus, or virally-infected cell, inhibits and/or prevents and/or destroys the growth of the target cell, virus, or virally-infected cell.

Such an ion having pharmacological properties is one which in the absence of an ion channel forming peptide is unable to cross a natural or synthetic lipid membrane; in particular a cell membrane, in sufficient amounts to affect a cell adversely.

The peptide and ion having pharmacological properties may be administered as a single composition or in separate compositions, and the single or separate compositions may include additional materials, actives and/or inactives, in addition to the peptide and ion having pharmacological properties. As representative examples of ions having pharmacological properties which may be employed, there may be mentioned fluoride, peroxide, bicarbonate, and silver ions.

The peptide and the ion having pharmacological properties, whether administered or prepared in a single composition or in separate compositions, are employed in amounts effective to inhibit and/or prevent and/or destroy the growth of the target cell, virus, or virally-infected cell. In effect, the ion potentiates the action of the peptide, i.e., the amount of ion is effective to reduce the minimum effective concentration of the peptide for inhibiting growth of a target cell, virus, or virally-infected cell.

The ion having pharmcological properties when used topically, is generally employed in a concentration of from 0.05% to 2.0%. When used systemically, the ion is generally employed in an amount of from 1 to 10 mg. per kg. of host weight. Peptide dosages may be within the ranges hereinabove described.

It is also to be understood that the peptide and ion having pharmacological properties may be delivered or administered in different forms; for example, the ion having pharamacological properties may be administered orally, while the peptide may be administered by IV or IP.

As representative examples of administering the peptide and ion having pharmcological properties for topical or local administration, the peptide could be administered in an amount of up to about 1% weight to weight and the ion having pharmacological properties delivered in an amount of about 50 mM (about 0.1%). Alternatively, the ion, in the form of a salt such as sodium fluoride, could be administered orally in conjunction with systemic administration of the peptide. For example, the peptide may be administered IV or IP to achieve a serum dose of 100 micrograms per milliliter (10 milligrams per kilogram) in conjunction with an oral dose of ion, in particular, sodium fluoride, of 10 meq per kilogram.

In accordance with another embodiment, the peptides of the present invention may be administered to a host in combination with an antibiotic selected from the class consisting of bacitracins, gramacidin, polymyxin, vancomycin, teichoplanin, aminoglycosides, hydrophobic antibiotics, penicillins, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, kanamycin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-O-methyl-1-4"-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-O-alpha-L-cladinosyl moiety, such as 3-O-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The peptide and antibiotic may be adminstered by direct administration to a target cell or by systemic or topical administration to a host which includes the target cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Peptide dosages may be those as hereinabove described.

As representative examples of administering the peptide and antibiotic for topical or local administration, the peptide could be administered in an amount of from about 0.1% to about weight to weight, and the antibiotic is delivered in an amount of from about 0.1% to about 10% weight to weight.

In accordance with another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents may also have anti-fungal activity, and that certain anti-fungal agents may have anti-parasitic activity.

In accordance with another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the peptides of the present invention may be administered for the purpose hereinabove described in combination with other biologically active amphiphilic peptides, or in combination with ion channel-forming proteins.

Examples of biologically active amphiphilic peptides which may be employed in combination with the peptides of the present invention include magainin peptides, PGLa peptides, XPF peptides, CPF peptides, cecropins and sarcotoxins.

A magainin peptide is either a magainin such as magainin I, II, or III or an analogue or derivative thereof.

The magainin peptides generally include at least fourteen amino acids. A magainin peptide preferably has 22 or 23 amino acids.

As representative examples of such magainin peptides, there may be mentioned peptides having the following peptide sequences as listed in the accompanying sequence listing:

(a) ($NH_2$) (SEQ ID. NO: 69)(OH) or ($NH_2$) (Magainin I)

(b) ($NH_2$) (SEQ ID. NO: 70)(OH) or ($NH_2$) (Magainin II)

(c) ($NH_2$) (SEQ ID. NO. 71)(OH) or ($NH_2$) (Magainin III)

The following are examples of peptide derivatives or analogues:

(d) ($NH_2$) (SEQ ID. NO: 72) (OH) or ($NH_2$)

(e) ($NH_2$) (SEQ ID. NO: 73) (OH) or ($NH_2$)

(f) ($NH_2$) (SEQ ID. NO: 74) (OH) or ($NH_2$)

Magainin peptides are described in *Proc. Natl. Acad. Sci.*, Vol. 84, pgs. 5449–53 (Aug. 1987). The term "magainin peptides" as used herein refers to the magainin peptides as well as derivatives and analogues thereof including but not limited to the representative derivatives and analogues.

A PGLa peptide is either PGLa or an analogue or derivative thereof.

The PGLa peptides generally include at least seventeen amino acids and may include as many as forty amino acids.

An XPF peptide is either XPF or an analogue or derivative thereof. The XPF peptides generally include at least nineteen amino acids and may include up to forty amino acids.

As representative examples of PGLa and XPF peptides, there may be mentioned the following peptide sequences as well as appropriate analogues and derivatives thereof:

PGLa: (SEQ ID NO: 75) ($NH_2$)

XPF: (SEQ ID NO: 76)

A review of XPF and PGLa can be found in Hoffman, et al., *EMBO J.*, 2:711–714 (1983); Andreu, et al., *J. Biochem*, 149:531–535 (1985); Gibson, et al., *J. Biol. Chem.*, 261: 5341–5349 (1986); and Giovannini, et al., *Biochem J.*, 243:113–120 (1987).

A CPF peptide is either a CPF peptide or an analogue or derivative thereof. In general, a CPF peptide does not include more than 40 amino acids.

Representative examples of CPF peptides which may be employed in combination with the peptides of the present invention, some of which have been described in the literature, include the following sequences:

(I) (SEQ ID NO: 77)

(II) (SEQ ID NO: 78)

(III) (SEQ ID NO: 79)

(IV) (SEQ ID NO: 80)

(V) ( SEQ ID NO: 81)

(VI) (SEQ ID NO: 82)

(VII) (SEQ ID NO: 83)

(VIII) (SEQ ID NO: 85)

(IX) (SEQ ID NO: 85)

(X) (SEQ ID NO: 86)

(XI) (SEQ ID NO: 87)

(XII) (SEQ ID NO: 88)

(XIII) (SEQ ID NO: 89)

The above is expressed as single letter code for amino acids.

A review of the CPF peptides can be found in Richter, K., Egger, R., and Kreil (1986) J. Biol. Chem. 261, 3676–3680; Wakabayashi, T. Kato, H., and Tachibaba, S. (1985) Nucleic Acids Research 13, 1817–1828; Gibson, B. W., Poulter, L., Williams, D. H., and Maggio, J. E. (1986) J. Biol. Chem. 261, 5341–5349.

The term cecropins includes the basic structure as well as analogues and derivatives thereof. The cecropins and analogues and derivatives thereof are described in Ann. Rev. Microbiol. 1987, Vol. 41, pages 103–26, in particular page 108, and in Christensen, et al., PNAS Vol. 85, pgs. 5072–76, which are hereby incorporated by reference.

The term sarcotoxins includes the basic materials as well as analogues and derivatives thereof. The sarcotoxins and analogues and derivatives thereof are described in Molecular Entomology, pages 369–78, in particular page 375, Alan R. liss, Inc. (1987), which is hereby incorporated by reference.

Ion channel-forming proteins or peptides which may be employed in combination with the peptides of the present invention include defensins, also known as human neutrophil antimicrobial peptides (HNP), major basic protein (MBP) of eosinophils, bactericidal permeability-increasing protein (BPI), and a pore-forming cytotoxin called variously perforin, cytolysin, or pore-forming protein. Defensins are described in Selsted, et al., *J. Clin. Invest.*, Vol. 76, pgs. 1436–1439 (1985). MBP proteins are described in Wasmoen, et al., *J. Biol. Chem.*, Vol. 263, pgs 12559–12563. (1988). BPI proteins are described in Ooi, et al, *J. Biol. Chem.*, Vol. 262, pgs. 14891–14894 (1987). Perforin is described in Henkart, et al., *J. Exp. Med.*, 160: 75 (1984), and in Podack, et al., *J. Exp. Med.*, 160:695 (1984). The above articles are hereby incorporated by reference.

The term ion channel-forming proteins includes the basic structures of the ion channel-forming proteins as well as analogues and derivatives.

The invention will now be further described with respect to the following examples; however, the scope of the present invention is not to be limited thereby.

EXAMPLE 1

Antibacterial Assay

The procedure for the following antibacterial assay is based upon the guidelines of the National Committee for Clinical Laboratory Standards, Document M7-T2, Volume 8, No. 8, 1988.

Stock solutions of the following Peptides (SEQ ID NO: 1) through (SEQ ID NO: 68) in accordance with the present invention are prepared at a concentration of 512 μg/ml in sterile deionized distilled water and stored at −70° C. The peptides are C-terminal amides.

Peptide (1A) is of the same structural formula as Peptide (SEQ ID NO: 1), except that each amino acid residue is a D-amino acid residue.

The stock peptide solution is diluted in serial dilutions (1:2) down the wells of a microtiter plate so that the final concentrations of peptides in the wells are 0.25, 0.50, 1, 2, 4, 8, 16, 32, 64, 128, and 256 μg/ml. 1–5×10$^5$ CFUs/ml of either *S. aureus* ATCC 25923, *E. coli* ATCC 25922, or *P. aeruginosa* ATCC 27853 were added to the wells in full strength Mueller Hinton broth (BBL 11443) from a mid-log culture. The inoculum is standardized spectrophotometrically at 600nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate. The results are given in Table I below. For purposes of explanation of Table I below, S is the MIC of the peptide against *S. aureus*, P is the MIC of the peptide against *P. aeruginosa*, and E is the MIC of the peptide against *E.coli.*

TABLE I

| Peptide | MIC (μg/ml) | | |
|---|---|---|---|
| | S | P | E |
| (SEQ ID NO:1) | 4,8 | 16,32 | 2,4 |
| (1A) | 2,4 | 32 | 2 |
| (SEQ ID NO:2) | 8,16 | 64 | 2,4 |
| (SEQ ID NO:3) | 256 | 64 | 32 |
| (SEQ ID NO:4) | 16 | 32 | 8 |
| (SEQ ID NO:5) | 32 | 32 | 4,16 |
| (SEQ ID NO:6) | 128 | 256 | 256 |
| (SEQ ID NO:7) | 128 | >256 | 256 |
| (SEQ ID NO:8) | 8 | 128 | 16 |
| (SEQ ID NO:9) | 16 | 32 | 8,16 |
| (SEQ ID NO:10) | 32 | >256 | 64 |
| (SEQ ID NO:11) | 16,32 | 64,128 | 8 |
| (SEQ ID NO:12) | 32 | 16,32 | 8 |
| (SEQ ID NO:13) | 32 | 64 | 16 |
| (SEQ ID NO:14) | 32 | 64 | 16 |
| (SEQ ID NO:15) | 4,8 | 8 | 4,8 |
| (SEQ ID NO:16) | 16 | 32 | 4 |
| (SEQ ID NO:17) | 16 | 64 | 16 |
| (SEQ ID NO:18) | 4,8 | 32,64 | 4 |
| (SEQ ID NO:19) | 16 | 64 | 4,8 |
| (SEQ ID NO:20) | 8 | 32 | 2,4 |
| (SEQ ID NO:21) | 128,256 | 128 | 32 |
| (SEQ ID NO:22) | 128 | 128 | 8 |
| (SEQ ID NO:23) | 32,64 | 64 | 32 |
| (SEQ ID NO:24) | 32 | 64 | 32 |
| (SEQ ID NO:25) | 128 | 128 | 16 |
| (SEQ ID NO:26) | 128 | >256 | 256 |
| (SEQ ID NO:27) | 32 | 64 | 4 |
| (SEQ ID NO:28) | 128 | 128 | 32 |
| (SEQ ID NO:29) | 32 | 64,128 | 8 |
| (SEQ ID NO:30) | 16 | 64,128 | 8 |
| (SEQ ID NO:31) | 256 | 256 | 32 |
| (SEQ ID NO:32) | 64,128 | 128 | 32 |
| (SEQ ID NO:33) | 64 | 128 | 4 |
| (SEQ ID NO:34) | 32 | 64 | 8 |
| (SEQ ID NO:35) | 32 | 128 | 8,16 |
| (SEQ ID NO:36) | 32 | 64 | 8,16 |
| (SEQ ID NO:37) | 4,8 | 16,32 | 2,4 |
| (SEQ ID NO:38) | 8 | 16 | 2 |
| (SEQ ID NO:39) | 16 | 64,128 | 8 |
| (SEQ ID NO:40) | 4,8 | 32,64 | 4 |
| (SEQ ID NO:41) | 64 | >256 | 128 |
| (SEQ ID NO:42) | 16 | 256 | 64 |
| (SEQ ID NO:43) | 4 | 8 | 4 |
| (SEQ ID NO:44) | 4 | 8 | 2 |
| (SEQ ID NO:45) | 16 | 64 | 4 |
| (SEQ ID NO:46) | 16 | 64 | 8 |
| (SEQ ID NO:47) | 4 | 32,64 | 4 |
| (SEQ ID NO:48) | 4,8 | 128 | 8 |
| (SEQ ID NO:49) | 32 | 16 | 4,8 |
| (SEQ ID NO:50) | 64 | 64 | 8 |
| (SEQ ID NO:51) | 2,4 | 32 | 2 |
| (SEQ ID NO:52) | 16 | 32 | 8,16 |
| (SEQ ID NO:53) | 16 | 64 | 4 |
| (SEQ ID NO:54) | 16 | 32 | 4 |
| (SEQ ID NO:55) | 16 | 32 | 4 |
| (SEQ ID NO:56) | 8 | 32 | 2,4 |
| (SEQ ID NO:57) | 4 | 64 | 4,8 |
| (SEQ ID NO:58) | 8 | 128 | 4,8 |
| (SEQ ID NO:59) | 8 | 128 | 8 |
| (SEQ ID NO:60) | 16 | 32 | 2 |
| (SEQ ID NO:61) | 2,4 | 32,64 | 4,8 |
| (SEQ ID NO:62) | 4 | 16 | 4 |
| (SEQ ID NO:63) | 4,8 | 8,16 | 4,8 |

TABLE I-continued

| Peptide | MIC (μg/ml) | | |
| --- | --- | --- | --- |
|  | S | P | E |
| (SEQ ID NO:64) | 4 | 4 | 4 |
| (SEQ ID NO:65) | 32 | 128,256 | 8,16 |
| (SEQ ID NO:66) | 16 | 128 | 8 |
| (SEQ ID NO:67) | 16 | 128 | 4,8 |
| (SEQ ID NO:68) | 16,32 | 32,64 | 8,16 |

EXAMPLE 2

Antiparasitic Assay

Logarithmic phase axenic cultures of *Acanthamoeba polyphaga* trophozoites were grown at 30° C. in fluid ppyg medium (2% proteose-peptone; 0.5% yeast extract; 0.5% glucose; pH 7.2). Cells were counted using a Coulter counter, and added to fresh ppyg medium to give a cell concentration of approximately 10,000 amoebas/ml. Cell suspensions were then transferred to Corning tissue culture flasks (25 cm$^3$) to which either Peptide (SEQ ID NO:1) or Peptide (SEQ ID NO:44) had been added to appropriate concentrations, with each flask containing 10ml of medium. The flasks were incubated at 30° C. 0.5ml samples were removed from the flasks, generally over a 5-day period, for counting in a Coulter Counter.

For determination of Minimum Inhibitory Concentration (MIC) and Minimum Amoebicidal Concentration (MAC) of the trophozoites, the contents of appropriate flasks were centrifuged, washed free of "old" medium and peptide with dilute saline, resuspended in fresh ppyg medium, and transferred to Corning tissue culture tubes (16×125 mm). The tubes were incubated at 30° C., and examined at daily intervals for growth of amoebas. Minimum Amoebicidal Concentration is defined is the minimum concentration of peptide necessary to kill the trophozoites. The results are given in Table II below.

TABLE II

| Antiparasitic Activity Against *Acanthamoeba polyphaga* | | |
| --- | --- | --- |
|  | Trophozoites | |
| Peptide | MIC | MAC |
| (SEQ ID NO:1) | 20 | 25 |
| (SEQ ID NO:44) | 25 | 40 |

The peptides of the present invention, whether administered alone or in combination with agents such as toxic ions, antibotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptide and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptide may be administered to a host in particular an animal, in an effective antibiotic and/or anti-tumor and/or antiviral and/or antimicrobial and/or antispermicidal and/or antifungal and/or antiparasitic amount, or in an amount effective to stimulate wound healing in a host. The peptides may be administered either alone or in combination with a toxic ion, antibiotic, or ion channel forming peptide or protein as hereinabove described. When the peptide is administered in combination with an ion having pharamacological properties, the activity of the peptide is potentiated.

When the peptide is administered in combination with an agent as hereinabove described, it is possible to administer the peptide and agent in separate forms. For example, the agent may be administered systemically and the peptide may be administered topically.

When the peptide is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide may also be employed in combination with a toxic ion as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The peptide and toxic ion may be used to inhibit, prevent, or destroy the growth of *Streptococcus mutans,* which is associated with dental caries and periodontal disease.

Numerous modifications and variations of the present invention are possible in light of the above teachings and, therefore, within the scope of the accompanying claims, the invention may be practiced other than as particularly described.

What is claimed is:

1. A biologically active amphiphilic peptide wherein said peptide has the following structural formula:

(Lys Ile Ala Gly Lys Ile Ala)$_3$—NH$_2$ (SEQ ID NO:1).

2. A biologically active amphiphilic peptide wherein said peptide has the following structural formula:

(Lys Ile Ala Lys Ile Ala Gly)$_3$-NH$_2$ (SEQ ID NO:2).

3. A peptide having the following structural formula:

Lys Leu Ala Ser Lys Ala Gly Lys Ile Ala Gly Lys Ile Ala Lys Val Ala Leu Lys Ala Leu—NH$_2$ (SEQ ID NO:44).

4. A peptide having the following structural formula:

Lys Ile Ala Gly Lys Ile Ala Lys Ile Ala Gly Orn Ile Ala Lys Ile Ala Gly Lys Ile (SEQ ID NO:45).

5. A peptide having the following structural formula:

(Lys Ile Ala Lys Lys Ile Ala)$_3$—NH$_2$ (SEQ ID NO:62).

6. A peptide having the following structural formula:

(Lys Phe Ala Lys Lys Phe Ala)$_3$—NH$_2$ (SEQ ID NO:63).

7. A peptide having the following structural formula:

(Lys Phe Ala Lys Lys Ile Ala)$_3$—NH$_2$ (SEQ ID NO:64).

8. A peptide selected from the group consisting of:

(SEQ ID NO:65)—NH$_2$
(SEQ ID NO:66)—NH$_2$
(SEQ ID NO:67)—NH$_2$; and
(SEQ ID NO:68)—NH$_2$.

* * * * *

UNITED STATES PATENT AND TRADEMARK OFFICE
CERTIFICATE OF CORRECTION

PATENT NO. : 5,459,237
DATED : October 17, 1995
INVENTOR(S) : Berkowitz et al.

It is certified that error appears in the above-indentified patent and that said Letters Patent is hereby corrected as shown below:

Claim 3, column 73, line 60; claim 5, column 74, line 51; claim 6, column 74, line 53; claim 7, column 74, line 55, "SEO" should read --SEQ--.

Signed and Sealed this

Ninth Day of January, 1996

Attest:

*Attesting Officer*

BRUCE LEHMAN

*Commissioner of Patents and Trademarks*